United States Patent
Savio et al.

(10) Patent No.: US 11,376,360 B2
(45) Date of Patent: Jul. 5, 2022

(54) FLUID INJECTOR AND PATIENT SET THEREFOR

(71) Applicant: BAYER HEALTHCARE LLC, Whippany, NJ (US)

(72) Inventors: Damian Peter Francis Savio, Lane Cove (AU); Peter Sprada, Croydon (AU); Eric Siu, Strathfield (AU); Barry Iddon, Jeannette, PA (US); Bipin Salunkhe, Cranberry Township, PA (US); Michael A. Spohn, Fenelton, PA (US); Richard Sokolov, Earlwood (AU); Matthew J. Leroch, Pittsburgh, PA (US); Michael McDermott, Pittsburgh, PA (US); Kevin P. Cowan, Allison Park, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 693 days.

(21) Appl. No.: 16/316,810

(22) PCT Filed: Jul. 17, 2017

(86) PCT No.: PCT/US2017/042314
§ 371 (c)(1),
(2) Date: Jan. 10, 2019

(87) PCT Pub. No.: WO2018/017447
PCT Pub. Date: Jan. 25, 2018

(65) Prior Publication Data
US 2019/0224407 A1    Jul. 25, 2019

Related U.S. Application Data

(60) Provisional application No. 62/363,668, filed on Jul. 18, 2016.

(51) Int. Cl.
*A61M 5/14* (2006.01)
*A61M 5/00* (2006.01)
(Continued)

(52) U.S. Cl.
CPC .......... *A61M 5/1408* (2013.01); *A61M 5/007* (2013.01); *A61M 5/16827* (2013.01); *A61M 5/20* (2013.01); *A61M 5/14546* (2013.01)

(58) Field of Classification Search
CPC ...... A61J 1/2003–2017; A61M 5/1408; A61M 5/16827
See application file for complete search history.

(56) References Cited

U.S. PATENT DOCUMENTS

| 3,886,937 A | 6/1975 | Bobo et al. |
| 4,425,113 A | 1/1984 | Bilstad et al. |

(Continued)

FOREIGN PATENT DOCUMENTS

| CA | 2842233 A1 | 1/2013 |
| EP | 2583716 A1 | 4/2013 |

(Continued)

OTHER PUBLICATIONS

"Extended European Search Report in EP Application No. 15806874", dated Dec. 7, 2017.
(Continued)

*Primary Examiner* — Nathan R Price
*Assistant Examiner* — Courtney B Fredrickson
(74) *Attorney, Agent, or Firm* — Joseph L. Kent; David Schramm; James R. Stevenson

(57) ABSTRACT

A syringe manifold (300) for a fluid injector assembly includes a middle body member (304) defining an upper cavity (308) and a lower cavity (309), the middle body member defining at least one fluid path in an upper surface of the middle body member and at least one fluid path in a
(Continued)

lower surface of the middle body member, the middle body member defining at least two ports extending through the middle body member, the middle body member comprising an outlet (302) for connection of the syringe manifold to at least one fluid delivery device; a lower body member (303) received within the lower cavity of the middle body member, the lower body member comprising at least one connector for connection of the lower body member to a syringe assembly (700); and an upper body member (305) received within the upper cavity of the middle body member.

16 Claims, 31 Drawing Sheets

(51) Int. Cl.
  *A61M 5/168* (2006.01)
  *A61M 5/20* (2006.01)
  *A61M 5/145* (2006.01)

(56) References Cited

U.S. PATENT DOCUMENTS

| | | | |
|---|---|---|---|
| 4,447,230 | A | 5/1984 | Gula et al. |
| 4,821,996 | A | 4/1989 | Bellotti et al. |
| 5,383,858 | A | 1/1995 | Reilly et al. |
| 6,428,518 | B1 * | 8/2002 | Brengle .............. A61M 5/1408 604/191 |
| 6,652,489 | B2 | 11/2003 | Trocki et al. |
| 7,094,216 | B2 | 8/2006 | Trombley et al. |
| 7,553,294 | B2 | 6/2009 | Lazzaro et al. |
| 7,556,619 | B2 | 7/2009 | Spohn et al. |
| 7,666,169 | B2 | 2/2010 | Cowan et al. |
| 8,147,464 | B2 | 4/2012 | Spohn et al. |
| 8,337,456 | B2 | 12/2012 | Schriver et al. |
| 8,540,698 | B2 | 9/2013 | Spohn et al. |
| 9,173,995 | B1 | 11/2015 | Tucker et al. |
| 9,199,033 | B1 | 12/2015 | Cowan et al. |
| 9,259,527 | B2 | 2/2016 | Spohn et al. |
| 9,480,797 | B1 | 11/2016 | Swantner et al. |
| 9,526,829 | B2 | 12/2016 | Spohn et al. |
| 2002/0087126 | A1 | 7/2002 | Quah |
| 2004/0064041 | A1 | 4/2004 | Lazzaro et al. |
| 2005/0113754 | A1 | 5/2005 | Cowan et al. |
| 2006/0100578 | A1 | 5/2006 | Lieberman et al. |
| 2009/0275829 | A1 | 11/2009 | Agarwal et al. |
| 2010/0113924 | A1 | 5/2010 | Hajicek et al. |
| 2011/0092828 | A1 | 4/2011 | Spohn et al. |
| 2012/0123257 | A1 | 5/2012 | Stokes, Jr. et al. |
| 2013/0102975 | A1 | 4/2013 | Lamb |
| 2014/0027009 | A1 | 1/2014 | Riley et al. |
| 2014/0060655 | A1 | 3/2014 | Ramos et al. |
| 2017/0056603 | A1 | 3/2017 | Cowan et al. |

FOREIGN PATENT DOCUMENTS

| | | |
|---|---|---|
| WO | 0132235 A2 | 5/2001 |
| WO | 2011066865 A1 | 6/2011 |
| WO | 2012155035 A1 | 11/2012 |
| WO | 2013010572 A1 | 1/2013 |
| WO | 2014047626 A2 | 3/2014 |
| WO | 2015106107 A1 | 7/2015 |
| WO | 2015164783 A1 | 10/2015 |
| WO | 2016172467 A1 | 10/2016 |
| WO | 2016191485 A1 | 12/2016 |
| WO | 2017091635 A1 | 6/2017 |
| WO | 2017091636 A1 | 6/2017 |
| WO | 2017091643 A1 | 6/2017 |

OTHER PUBLICATIONS

"International Preliminary Report on Patentability from PCT Application No. PCT/US2015/034656", dated Dec. 22, 2016.
"International Preliminary Report on Patentability from PCT Application No. PCT/US2017/042314", dated Jan. 31, 2019.
"International Search Report and the Written Opinion from PCT/US2015/034565", dated Sep. 15, 2015.
"International Search Report and Written Opinion from PCT Application No. PCT/US2017/042314", dated Dec. 13, 2017.
"Partial International Search Report from PCT Application No. PCT/US2017/042314", dated Oct. 19, 2017.

\* cited by examiner

FLUID INJECTOR AND PATIENT SET THEREFOR

CROSS REFERENCE TO RELATED APPLICATION

This application is a 371 national phase application of PCT International Application No. PCT/US2017/042314, filed Jul. 17, 2017, and claims the benefit of U.S. Provisional Patent Application No. 62/363,668, filed Jul. 18, 2016, the disclosures of which are incorporated herein by reference in their entirety.

BACKGROUND OF THE DISCLOSURE

Field of the Disclosure

The present disclosure relates generally to medical fluid delivery systems and apparatuses for delivering one or more medical fluids to a patient.

Description of Related Art

In many medical diagnostic and therapeutic procedures, a medical practitioner, such as a physician, injects a patient with one or more medical fluids. In recent years, a number of injector-actuated syringes and fluid injectors for pressurized injection of medical fluids, such as a contrast media solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of one or more fluids at a preset pressure and/or flow rate.

In some injection procedures, the medical practitioner places a catheter or a needle connected to tubing, or other fluid delivery connection into a vein or artery of the patient. The catheter or the tubing is connected to either a manual or a powered automatic fluid injection mechanism. Automatic fluid injection mechanisms typically include at least one syringe connected to a fluid injector having, for example, at least one powered linear piston. The at least one syringe may include a source of contrast and/or a source of flushing fluid. The medical practitioner enters settings into an electronic control system of the fluid injector for a fixed volume of contrast and/or saline, a fixed rate of injection for each, and specific times for injections of each of the one or more fluids.

The injected contrast and/or saline is delivered to a patient's vasculature through a catheter or needle inserted into the patient's body, such as the patient's arm or groin area. A dose of contrast is referred to as a bolus. Once the bolus of contrast is delivered to the desired site, that area is imaged using a conventional imaging technique, such as angiography imaging, CT imaging, ultrasound, MRI, PET or SPECT imaging, and/or other imaging procedures. The presence of the contrast becomes clearly visible against the background of the surrounding tissue.

Conventional injector design includes a controller, including buttons and readouts, located on the face of the injector assembly which requires the user or technician to enter and monitor the injection while remaining within arms-length of the injector assembly. Further, when filling the one or more syringes associated with the fluid injection system, the fluid containers are typically inverted and hung on an adjacent stand. However, there is a need for improved injector design that provides benefits and ease of use features to allow a user or technician to freely move throughout the treatment room and readily fill the one or more syringes. While various fluid injection systems and methods are known in the medical field, improved designs and methods for use of the fluid injector which improve the user experience continue to be in demand. Particularly, in view of the disadvantages of the existing fluid injection systems that limit user simplicity and experience, there is need for an improved fluid injection system that provides better user experience and improved workflow.

SUMMARY OF THE DISCLOSURE

Accordingly, it is an object of the present disclosure to provide systems for delivering fluid to a patient or multiple patients that overcome some or all of the deficiencies of the prior art.

According to one example of the present disclosure, a syringe manifold for a fluid injector assembly includes an upper body member, the upper body member comprising at least one fluid conducting element for piercing a fluid container; a middle body member defining an upper cavity and a lower cavity, the upper body member connected with the upper cavity of the middle body member, and the middle body member further comprising: at least one first fluid path defined in an upper surface of the middle body member; at least one second fluid path defined in a lower surface of the middle body member; at least one first port defined by the at least one first fluid path; at least one second port defined by the at least one first fluid path and the at least one second fluid path; and an outlet for connection of the syringe manifold to at least one fluid delivery device; and a lower body member connected with the lower cavity of the middle body member, the lower body member comprising at least one connector for connection of the lower body member to a syringe assembly, wherein the at least one first port on the middle body member establishes fluid communication between the at least one fluid conducting element and the at least one connector, and wherein the at least one first fluid path, the at least one second fluid path, and the at least one second port establish fluid communication between the at least one connector and the outlet of the middle body member.

In another example of the present disclosure, the at least one fluid conducting element comprises two spike members, and the lower body member comprises two connectors. The middle body member comprises two second fluid paths in the lower surface of the middle body member, and the middle body member defines two first ports and two second ports extending through the middle body member. The at least one first port is defined at a first end of the at least one second fluid path defined in the lower surface of the middle body member, and the at least one second port is defined at a second, opposing end of the at least one second fluid path defined in the lower surface of the middle body member. A check valve diaphragm is provided in each of the at least one first port and the at least one second port. A first check valve diaphragm positioned between the at least one fluid conducting element and the at least one connector permits fluid flow from the at least one fluid conducting element to the at least one connector and prevents fluid flow from the at least one connector to the at least one fluid conducting element, and a second check valve diaphragm positioned between the at least one connector and the outlet of the middle body member permits fluid flow from the at least one connector to the outlet and prevents fluid flow from the outlet to the at least one connector. A floating disc valve is provided in each of the at least one first port and the at least one second port. A first floating disc valve positioned between the at least one fluid conducting element and the at least one connector permits fluid flow from the at least one fluid conducting element to the at least one connector and prevents fluid flow from the at least one connector to the at least one fluid conducting element, and a second floating disc valve positioned between the at least one connector and the outlet of the middle body member permits fluid flow from the at least one connector to the outlet and prevents fluid flow from the outlet to the at least one connector. At least one of the upper body member and the lower body member are welded to the middle body member. A syringe may be connected to the at least one connector.

In another example of the present disclosure, a syringe manifold for a fluid injector assembly comprises: an upper body member, the upper body member comprising at least one fluid conducting element for piercing a fluid container; a middle body member defining an upper cavity and a lower cavity, the upper body member connected with the upper cavity of the middle body member, the middle body member further comprising: at least one fluid path in an upper surface of the middle body member; at least one first port defined by the at least one fluid path; and at least one second port defined by the at least one fluid path; and a lower body member connected with the lower cavity of the middle body member, the lower body member comprising: at least one connector for connection of the lower body member to a syringe assembly; at least one fluid path; and an outlet for connection of the syringe manifold to at least one fluid delivery device; wherein the at least one first port defined in the middle body member establishes fluid communication between the at least one fluid conducting element and the at least one connector, and wherein the at least one fluid path defined in the lower body member, the at least one first port defined in the middle body member, the at least one fluid path defined in the upper surface of the middle body member, and the at least one second port defined in the middle body establish fluid communication between the at least one connector and the outlet of the lower body member.

In another example of the present disclosure, the at least one fluid conducting element comprises two spike members, and the lower body member comprises two connectors. The lower body member comprises two fluid paths, and the middle body member comprises four ports extending through the middle body member. The at least one first port provided in the middle body member is positioned adjacent a first end of the at least one fluid path defined in the lower body member, and the at least one second port provided in the middle body member is positioned adjacent a second, opposing end of the at least one fluid path defined in the lower body member. A check valve diaphragm or floating disc valve is positioned between the at least one fluid conducting element of the upper body member and the at least one connector of the lower body member. A syringe is connected to the at least one connector.

In another example of the present disclosure, a syringe assembly comprises: a barrel extending from a conical distal end to a proximal end; an adapter connected to the distal end of the barrel, the adapter configured for connection to a connector of a syringe manifold; the syringe manifold comprising: an upper body member comprising at least one fluid conducting element for piercing a fluid container; a middle body member defining an upper cavity and a lower cavity, the upper body member connected with the upper cavity of the middle body member; and a lower body member connected with the lower cavity of the middle body member, the lower body member comprising at least one connector for connection of the lower body member to the adapter; and a flow directing assembly held within the distal end of the barrel and extending through the adapter, wherein the flow directing assembly is configured to direct fluid being drawn into the syringe assembly along an inner wall of the barrel.

In another example of the present disclosure, a portion of the flow directing assembly is held between a protrusion extending inwardly from an inner surface of the distal end and a proximal end of the adapter. The flow directing assembly comprises a main body member with at least one surface that is angled such that fluid being drawn into the syringe assembly is directed along an inner wall of the barrel. A plurality of locking features is provided on the proximal end of the barrel.

Further examples will now be described in the following numbered clauses.

Clause 1: A syringe manifold for a fluid injector assembly, the syringe manifold comprising: an upper body member, the upper body member comprising at least one fluid conducting element for piercing a fluid container; a middle body member defining an upper cavity and a lower cavity, the upper body member connected with the upper cavity of the middle body member, and the middle body member further comprising: at least one first fluid path defined in an upper surface of the middle body member; at least one second fluid path defined in a lower surface of the middle body member; at least one first port defined by the at least one first fluid path; at least one second port defined by the at least one first fluid path and the at least one second fluid path; and an outlet for connection of the syringe manifold to at least one fluid delivery device; and a lower body member connected with the lower cavity of the middle body member, the lower body member comprising at least one connector for connection of the lower body member to a syringe assembly, wherein the at least one first port on the middle body member establishes fluid communication between the at least one fluid conducting element and the at least one connector, and wherein the at least one first fluid path, the at least one second fluid path, and the at least one second port establish fluid communication between the at least one connector and the outlet of the middle body member.

Clause 2: The syringe manifold of Clause 1, wherein the at least one fluid conducting element comprises two spike members, and wherein the lower body member comprises two connectors.

Clause 3: The syringe manifold of Clause 2, wherein the middle body member comprises two second fluid paths in the lower surface of the middle body member, and wherein the middle body member defines two first ports and two second ports extending through the middle body member.

Clause 4: The syringe manifold of any of Clauses 1-3, wherein the at least one first port is defined at a first end of the at least one second fluid path defined in the lower surface of the middle body member, and wherein the at least one second port is defined at a second, opposing end of the at least one second fluid path defined in the lower surface of the middle body member.

Clause 5: The syringe manifold of any of Clauses 1-4, wherein a check valve diaphragm is provided in each of the at least one first port and the at least one second port.

Clause 6: The syringe manifold of Clause 5, wherein a first check valve diaphragm positioned between the at least one fluid conducting element and the at least one connector permits fluid flow from the at least one fluid conducting element to the at least one connector and prevents fluid flow from the at least one connector to the at least one fluid conducting element, and wherein a second check valve diaphragm positioned between the at least one connector and the outlet of the middle body member permits fluid flow from the at least one connector to the outlet and prevents fluid flow from the outlet to the at least one connector.

Clause 7: The syringe manifold of any of Clauses 1-6, wherein a floating disc valve is provided in each of the at least one first port and the at least one second port.

Clause 8: The syringe manifold of Clause 7, wherein a first floating disc valve positioned between the at least one fluid conducting element and the at least one connector permits fluid flow from the at least one fluid conducting element to the at least one connector and prevents fluid flow from the at least one connector to the at least one fluid conducting element, and wherein a second floating disc valve positioned between the at least one connector and the outlet of the middle body member permits fluid flow from the at least one connector to the outlet and prevents fluid flow from the outlet to the at least one connector.

Clause 9: The syringe manifold of any of Clauses 1-8, wherein at least one of the upper body member and the lower body member are welded to the middle body member.

Clause 10: The syringe manifold of any of Clauses 1-9, further comprising a syringe connected to the at least one connector.

Clause 11: A syringe manifold for a fluid injector assembly, the syringe manifold comprising: an upper body member; the upper body member comprising at least one fluid conducting element for piercing a fluid container; a middle body member defining an upper cavity and a lower cavity, the upper body member connected with the upper cavity of the middle body member, the middle body member further comprising: at least one fluid path in an upper surface of the middle body member; at least one first port defined by the at least one fluid path; and at least one second port defined by the at least one fluid path; and a lower body member connected with the lower cavity of the middle body member, the lower body member comprising: at least one connector for connection of the lower body member to a syringe assembly; at least one fluid path; and an outlet for connection of the syringe manifold to at least one fluid delivery device, wherein the at least one first port defined in the middle body member establishes fluid communication between the at least one fluid conducting element and the at least one connector, and wherein the at least one fluid path defined in the lower body member, the at least one first port defined in the middle body member, the at least one fluid path defined in the upper surface of the middle body member, and the at least one second port defined in the middle body establish fluid communication between the at least one connector and the outlet of the lower body member.

Clause 12: The syringe manifold of Clause 11, wherein the at least one fluid conducting element comprises two spike members, and wherein the lower body member comprises two connectors.

Clause 13: The syringe manifold of Clause 11 or 12, wherein the lower body member includes two fluid paths, and wherein the middle body member includes four ports extending through the middle body member.

Clause 14: The syringe manifold of any of Clauses 11-13, wherein the at least one first port provided in the middle body member is positioned adjacent a first end of the at least one fluid path defined in the lower body member, and wherein the at least one second port provided in the middle body member is positioned adjacent a second, opposing end of the at least one fluid path defined in the lower body member.

Clause 15: The syringe manifold of any of Clauses 11-14, further comprising a check valve diaphragm or floating disc valve positioned between the at least one fluid conducting element of the upper body member and the at least one connector of the lower body member.

Clause 16: The syringe manifold of any of Clauses 1-15, further comprising a syringe connected to the at least one connector.

Clause 17: A syringe assembly comprising: a barrel extending from a conical distal end to a proximal end; an adapter connected to the distal end of the barrel, the adapter configured for connection to a connector of a syringe manifold, the syringe manifold comprising: an upper body member comprising at least one fluid conducting element for piercing a fluid container; a middle body member defining an upper cavity and a lower cavity, the upper body member connected with the upper cavity of the middle body member; and a lower body member connected with the lower cavity of the middle body member, the lower body member comprising at least one connector for connection of the lower body member to the adapter; and a flow directing assembly held within the distal end of the barrel and extending through the adapter, wherein the flow directing assembly is configured to direct fluid being drawn into the syringe assembly along an inner wall of the barrel.

Clause 18: The syringe assembly of Clause 17, wherein a portion of the flow directing assembly is held between a protrusion extending inwardly from an inner surface of the distal end and a proximal end of the adapter.

Clause 19: The syringe assembly of Clause 17 or Clause 18; wherein the flow directing assembly comprises a main body member with at least one angled surface such that fluid being drawn into the syringe assembly is directed along an inner wall of the barrel.

Clause 20: The syringe assembly of any of Clauses 17-19, further comprising a plurality of locking features provided on the proximal end of the barrel.

Clause 21: The syringe assembly of any of Clauses 17-20, wherein the syringe manifold comprises at least one port defined in the middle body member to establish fluid communication between the at least one fluid conducting element and the at least one connector.

Clause 22: The syringe assembly of any of Clauses 17-21, wherein the middle body member of the syringe manifold defines at least one fluid flow path to establish fluid communication between the syringe assembly and an outlet defined by the syringe manifold.

While several examples of fluid injection and delivery systems are shown in the accompanying figures and described herein in detail, other examples will be apparent to, and readily made by, those skilled in the art without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive.

DETAILED DESCRIPTION

Figure 1:
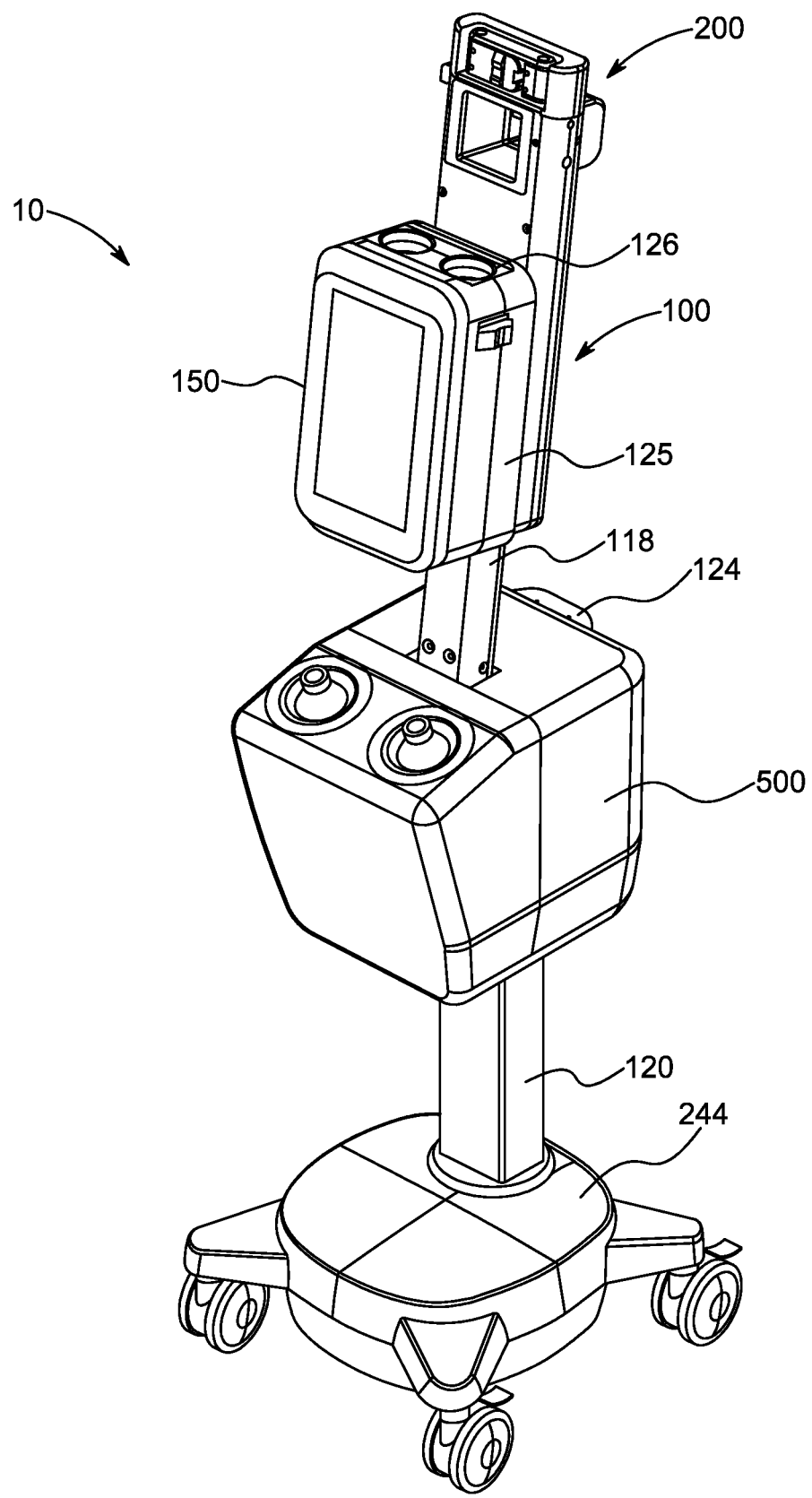
FIG. 1 is a front perspective view of a fluid delivery system according to an embodiment of the present disclosure.
Figure 2:
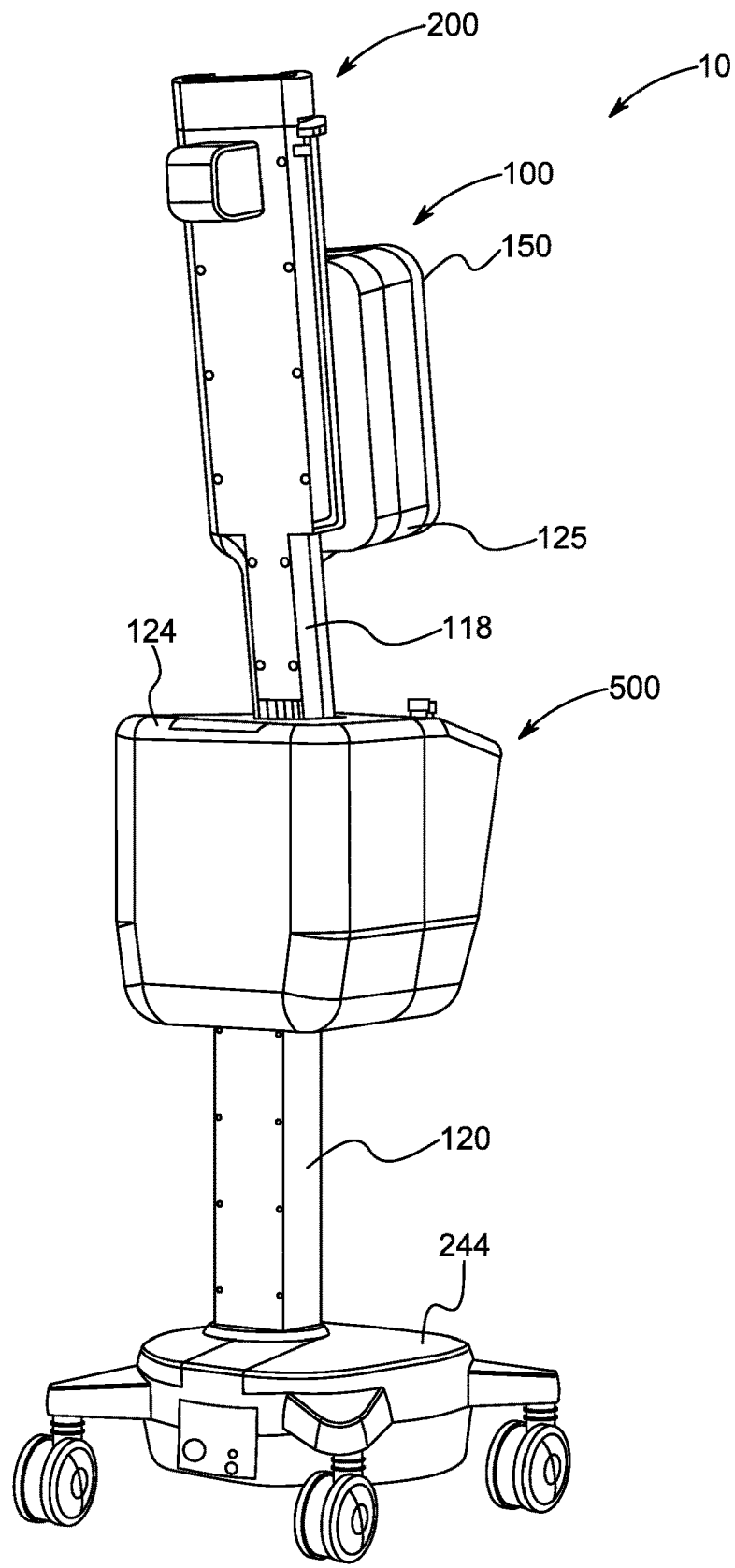
FIG. 2 is a rear perspective view of the fluid delivery system of FIG. 1 according to an embodiment.
Figure 3:
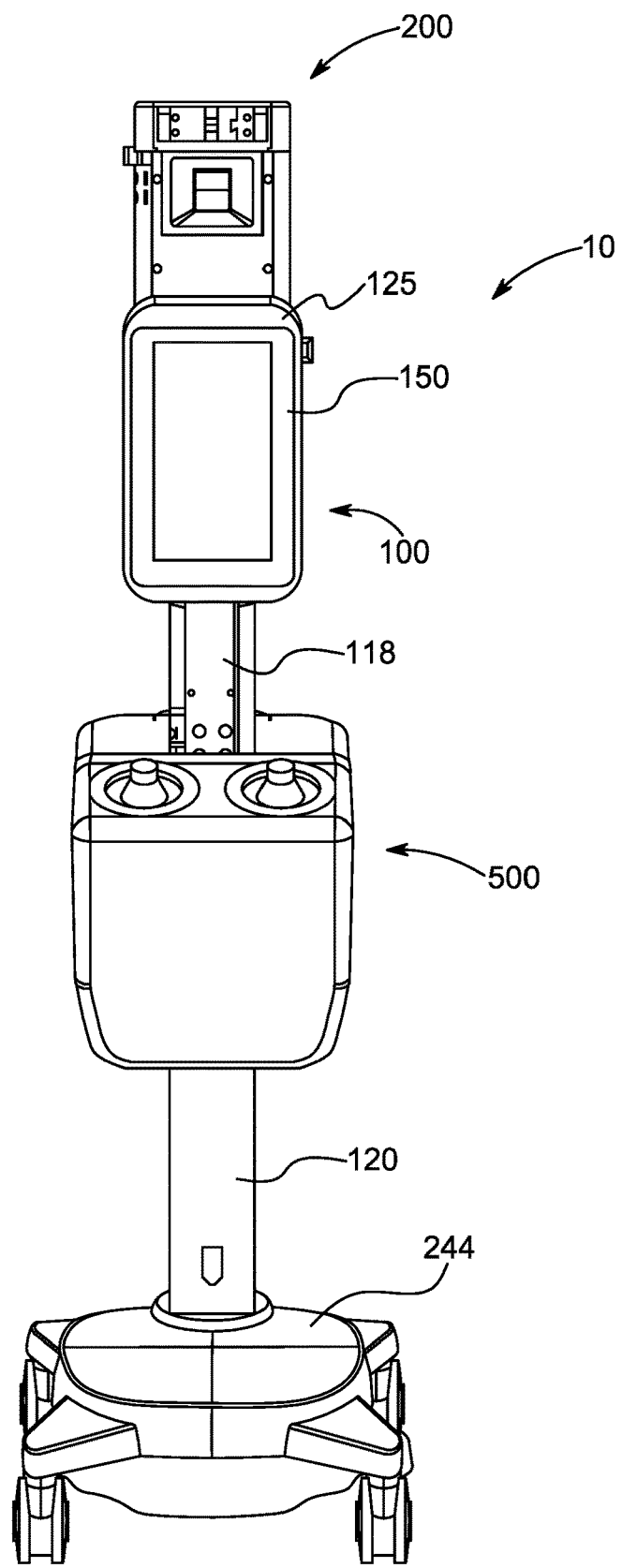
FIG. 3 is a front view of the fluid delivery system of FIG. 1 according to an embodiment.

For purposes of the description hereinafter, the terms "upper," "lower," "right," "left," "vertical," "horizontal," "top," "bottom," "lateral," "longitudinal," and derivatives thereof shall relate to the disclosure as it is oriented in the drawing figures. When used in relation to an injector, the term "proximal" refers to a portion of an injector furthest from a syringe port of an injector. The term "distal" refers to a portion of an injector closest to a syringe port of an injector. It is to be understood, however, that the disclosure may assume alternative variations and step sequences, except where expressly specified to the contrary. It is also to be understood that the specific devices and processes illustrated in the attached drawings, and described in the following specification, are simply illustrative examples of the disclosure. Hence, specific dimensions and other physical characteristics related to the examples (i.e., examples, variants, variations) disclosed herein are not to be considered as limiting. As used herein, the term "multi-patient use" means an article that can be utilized for injection procedures for multiple patients without cross-contamination of the portions of the multi-patient use article with biological fluids of different patients. As used herein, the term "single-patient use" means an article that is utilized for one or more injection procedures for a single patient, which is then disposed of after the one or more injection procedure on the single patient before preparation for injection of a second patient utilizing a new single-patient use article.

As used herein, the terms "communication" and "communicate" when used in reference to one or more computer processors, devices, units, or operating systems, refer to the receipt or transfer of one or more signals, messages, commands, or other type of data. For one unit or device to be in communication with one or more other unit or device means that the one unit or device is able to receive data from and/or transmit data to the one or more other unit or device. A communication may use a direct or indirect connection, and may be wired and/or wireless in nature. Additionally, two or more units or devices may be in communication with each other even though the data transmitted may be modified, processed, routed, etc., between the first and second unit or device. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. In non-limiting examples, a communication may occur through one or more wired or wireless connections, such as, through one or more wires, through direct wireless protocols such as Bluetooth, Near Field Communication (NFC), or other radio frequency protocols, and/or through indirect wireless communication such as through a local Wi-Fi network or secure Internet connection. Wireless communication may include, but is not limited to, any communication that does not require direct wired contact between the two communicating units or devices such as via a Wi-Fi network, communication via Bluetooth, NFC, or other conventional wireless system, or other non-wired electromagnetic communication systems. It will be appreciated that numerous other arrangements are possible.

In another non-limiting example, a fluid injection system is provided, having an injector assembly with at least one syringe port, a processor, and a wired or wirelessly connected controller, which may have a touch screen or other user input device, and/or a display configured for inputting one or more injection parameters and displaying one or more injection features. Suitable processors and/or controllers may include, but are not limited to, a central processing unit (CPU), a desktop or laptop computer, a tablet computer, a smartphone or a personal data assistant device, or other handheld computer processor. The processor may be in communication with the controller by a wired or wireless communication mechanism.

In additional examples, a fluid injection system may have an injector assembly with at least one syringe port and, optionally, a controller, wherein the injector assembly further includes a retractable pole or stowable stand configured to extend above the injector assembly and having at least one hanging feature or hook member for hanging at least one fluid container. The fluid container can be a saline bag or container, a multi-dose pharmaceutical liquid container, a container containing multiple doses of a contrast or imaging agent, a container containing a single dose of a contrast or imaging agent, and various combinations thereof.

Various examples of the present disclosure are directed to fluid injection systems for injecting one or more fluids into a patient during an injection procedure. The design and features of the fluid injection system provide ease of use and improved user experience, for example by allowing one or more of: closer monitoring of an injection procedure, the ability to move throughout an injection suite during the injection procedure while being able to control one or more parameters or features of the ongoing injection procedure, provide a fluid injection system that includes a portion suitable for use with multiple injection protocols, for example throughout a day (i.e., a multi-patient use portion), and a portion suitable for use for a single injection protocol before disposal (i.e., a single-patient use portion), provide a fluid injection system that can quickly fill one or more syringes with one or more medical fluids, for example from one or more multi-dose containers, prior to an injection protocol, provide a fluid injection system that can determine a fluid fill level in the one or more syringes and/or determine one or more properties of the fluid such as a fluid type in the one or more syringes, provide a manifold for connecting the one or more syringes to the one or more multi-dose containers and connect the one or more syringes to a fluid path set connecting the one or more syringes to a patient, to allow filling of the one or more syringes with the medical fluids and delivering the medical fluids to the patient in controlled volumes, doses and flow rates, as determined by a process and/or user input into the processor. Further features allow for hanging of one or more multi-dose fluid containers on the fluid injection system for ready access when filling and/or refilling the one or more syringes associated with the fluid injection system. In particular examples, the fluid injection systems of the present disclosure may be used for injection of one or more imaging agents in an imaging procedure, such as, for example CT scan, MRI, and other imaging procedures.

In specific examples, the fluid injector system may be a front-loading fluid injector system similar to the various examples of the injectors disclosed in U.S. Pat. Nos. 5,383,858, 7,553,294, 7,666,169, 9,173,995 9,199,033 and in International Patent Application Nos. PCT/US12/374891, PCT/US15/10825, PCT/US15/27582, PCT/US16/28824, PCT/US16/34140, and in U.S. Patent Application Publication No. 2014/0027009 and Ser. No. 14/925,722, and in U.S. Provisional Application Nos. 62/259,708, 62/259,891, 62/259,906, the disclosures of which are incorporated by reference in their entirety. Other examples may include new fluid injector systems designed to include various examples of the interface described herein.

FIGS. 1-4 illustrate a fluid injection system 10 including a controller 150 including a touch screen, according to a non-limiting example of the present disclosure. With reference to FIG. 1, a fluid delivery device or injector 100 (hereinafter referred to as "injector 100"), such as an automated or powered fluid injector, is adapted to interface with and actuate at least one syringe (not shown), which may be independently filled with a medical fluid, such as contrast media having a desired concentration or identity, saline solution, or other desired medical fluids. The injector 100 may be used during a medical procedure, such as an imaging procedure, to inject the medical fluid into the body of a patient from the at least one syringe (not shown) operated by a fluid control device (not shown), which may be at least partially internal to the injector 100. In non-limiting examples, the injector 100 may be a multi-syringe injector, wherein a plurality of syringes may be oriented side-by-side or in another arrangement and include plungers separately actuated by respective pistons associated with the injector 100, and controlled by the fluid control device. In one non-limiting example, two syringes may be arranged in a side-by-side fashion and filled with two different medical fluids, such as a contrast agent and a saline solution, and the injector 100 may be configured to deliver fluid to a patient from one or both of the syringes either sequentially or simultaneously. It will be appreciated that other arrangements are possible.

With continued reference to FIGS. 1-4, the injector 100 may have a housing 125 formed from a suitable structural material, such as plastic, a composite material, and/or metal. The housing 125 may be of various shapes and sizes depending on the desired application. For example, the fluid delivery system 10 may be a freestanding structure having one or more support portions 118 and 120 connected to a base 244 with one or more rollers or wheels such that the injector 100 is movable over the floor. The injector 100 may include at least one syringe port 126 for releasably connecting the at least one syringe to respective piston elements. In various examples, the at least one syringe includes at least one syringe retaining member (not shown) configured for retaining the syringe within the syringe port 126 of the injector 100. In non-limiting examples, the at least one syringe retaining member is configured to operatively engage a locking mechanism provided on or in the syringe port 126 of the injector 100 to facilitate self-oriented loading and/or removal of the syringe to and from the injector 100. The syringe retaining member and the locking mechanism together define a connection interface for connecting the syringe to the injector 100. Non-limiting examples of various connection interfaces are described in U.S. Pat. Nos. 9,173,995 and 9,199,033. In other embodiments, syringe port 126 may facilitate self-oriented loading and/or removal of a pressure jacket adapted for containing a compressible syringe or rolling diaphragm syringe, to and from the injector 100 for example as described in International Patent Application Nos. PCT/US15/57747 and PCT/US15/57751, the disclosures of which are incorporated in their entirety by this reference.

Figure 4:
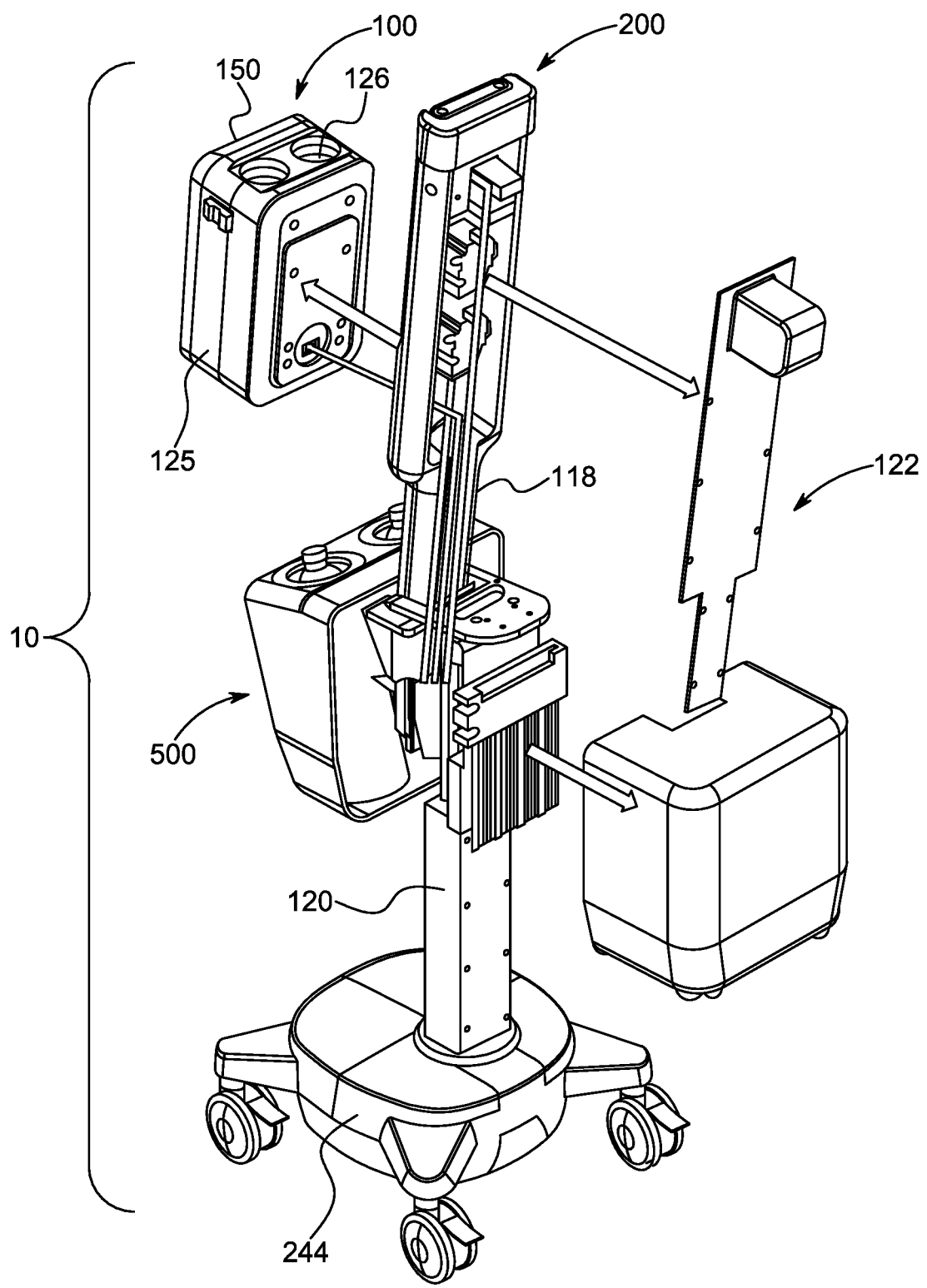
FIG. 4 is an exploded rear perspective view of the fluid delivery system of FIG. 1 according to an embodiment.

In certain non-limiting examples, it is desirable to temporarily rotate and/or invert the injector housing 125 including syringe ports between a substantially vertical position (i.e., with the syringe port(s) pointing upwards), which may facilitate, for example, the loading of a syringe into a syringe port and/or the filling of a syringe with medical fluid, and an inverted position, which may facilitate, for example, minimization of air bubbles in a medical fluid contained within a syringe from entering the fluid path, or the conducting of an injection procedure. Accordingly, in non-limiting examples of the present disclosure, the housing 125 may be connected to the support portion 118 in a rotatable fashion such that the housing 125 is rotatable relative to the support portion 118 and retractable pole 200. As shown in FIG. 4, the housing 125 may be removable from the injector 100. Further, a rear access cover 122 may be removably connected to a rear surface of the components of the injector 100. The rear access cover 122 may be removed by a technician to access the inner electronics, mechanical features, and cables of the injector 100 for repair or replacement. The rear access cover 122 may be a single component or several separate cover components.

Figure 6:
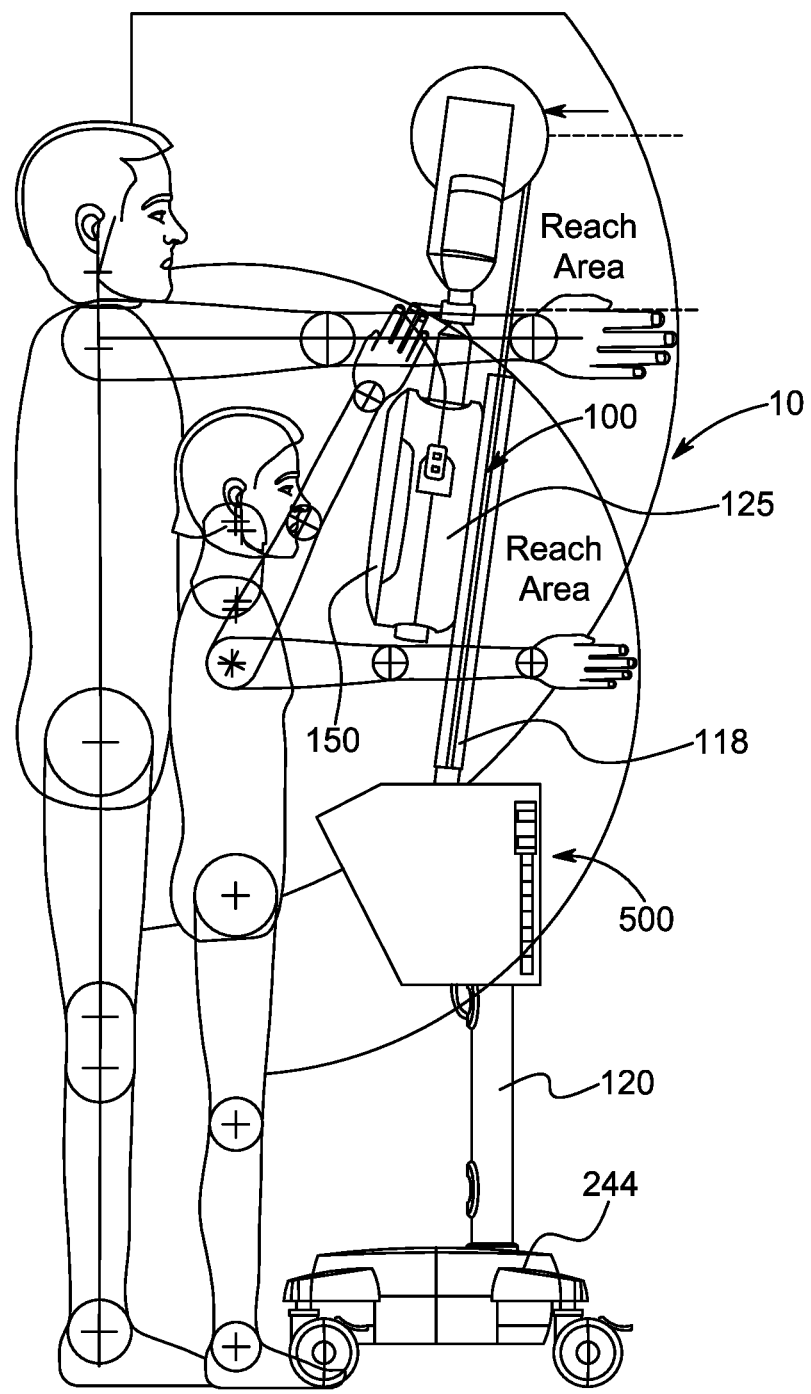
FIG. 6 is an illustration of a side view of the fluid delivery system of FIG. 1 according to an embodiment showing reach areas of different users.
Figure 7:
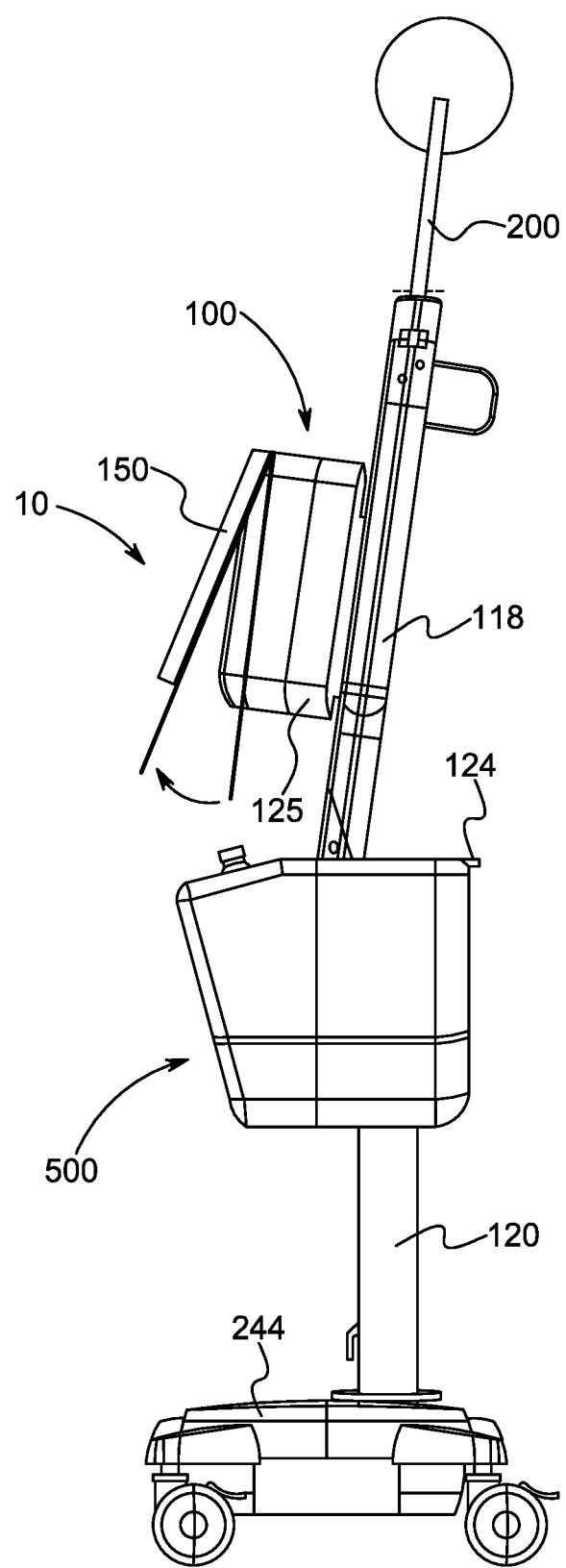
FIG. 7 is a side view of the fluid delivery system of FIG. 1 according to an embodiment set at a maximum height.
Figure 8:
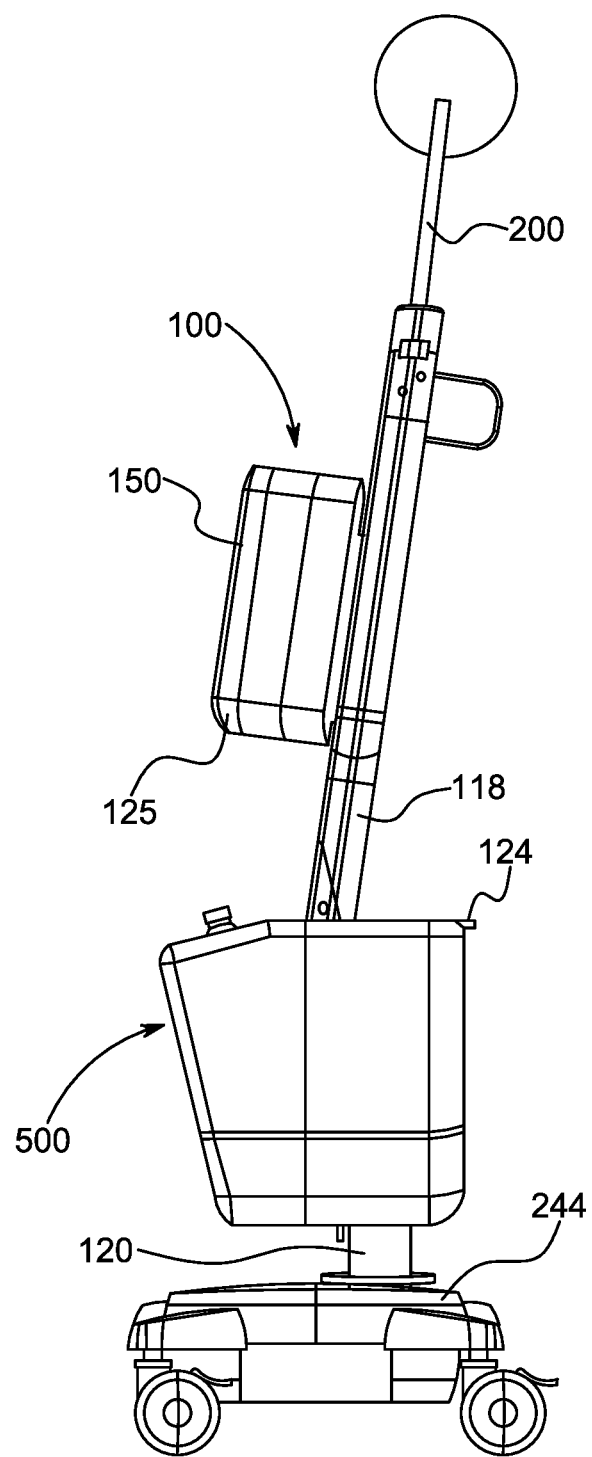
FIG. 8 is a side view of the fluid delivery system of FIG. 1 according to an embodiment set at a minimum height.

As shown in FIGS. 6-8, a lower support member 120 may be extended or retracted in a vertical direction to adjust the height of the fluid delivery system 10 depending, for example, on the operator height and/or reach area (see FIG. 6). An operator may push down on a handle 124 to release a locking connection between the lower support member 120 and a fluid warmer 500 (described in greater detail herein) provided on the lower support member 120. As the handle 124 is pressed down, the operator can lift or lower the fluid warmer 500 and associated injector stand 118 to adjust the height of the injector 100. A hydraulic lift (not shown) may be provided in the lower support member 120 to assist in adjusting the height of the fluid delivery system 10. The lower support member 120 may include a plurality of members that are arranged in a telescopic manner to allow adjustment of the height of the fluid delivery system 10. In one example, the height of the injector 100 may be adjusted up to 250 mm or more, for example the height may be adjusted from 0 to 500 mm, or in other embodiments from 0 to 400 mm, and in other embodiments from 0 to 250 mm. A maximum height of the fluid delivery system 10 is depicted in FIG. 7. A minimum height of the fluid delivery system 10 is depicted in FIG. 8.

In non-limiting examples, at least one fluid path set (not shown) may be fluidly connected with the distal end of the at least one syringe for delivering medical fluid from the at least one syringe to a catheter, needle, or other fluid delivery connection (not shown) inserted into a patient at a vascular access site. Fluid flow from the at least one syringe may be regulated by a fluid control module operated by a controller or processor, such as a detachable touch screen controller 150 or any suitable device. The fluid control module may operate various, pistons, valves, and/or flow regulating devices to regulate the delivery of the medical fluid, such as saline solution and contrast, to the patient based on one or more user selected injection parameters or standard injection protocols, such as injection flow rate, duration, total injection volume, and/or ratio of contrast media and saline.

Having generally described the structure and function of the fluid delivery system 10, the various features associated with the present disclosure will now be described in reference to the Figures. FIGS. 1-4 illustrate an injector 100 according to a non-limiting example of the present disclosure. The injector 100 may include an internal fluid control device (not shown) which may be controlled by the controller 150.

The controller 150 may include one or more processors, memory, network interfaces, and/or the like and may be configured to generate a display comprising a graphical user interface ("GUI") (shown in FIG. 5), which may allow a user to view and/or interact with various injection parameters through graphical icons and visual indicators produced on the display. In non-limiting examples, the controller 150 may be formed as a detachable touch screen controller. The controller 150 may also be non-removably attached to the injector 100. The controller 150 may be used to monitor one or more injection parameters, including, for example, patient specific information (age, weight, sex, organ to be imaged, dosage of imaging agent, etc.), which may be inputted by the user or recalled/downloaded from a database, a network, a memory, or another controller in communication with the system by a wired or wireless communication process. The controller 150 may be further configured to control various injection parameters which may be inputted by a user and/or calculated by one or more algorithmic calculations performed by the controller 150, the fluid control device, and/or another controller or processor in communication with the fluid control device and/or the controller 150 based on data downloaded from a database and/or inputted by a user. Alternatively, the controller 150 may be in communication with one or more other processors, where one or more of the injection parameters may be inputted or stored and then communicated to controller 150 by either a wired or wireless communication interface.

Various user selected injection parameters 170 (see FIG. 5) and injection instructions, such as injection flow rate, injection start time, duration, total injection volume of each of the one or more fluids, remaining volume to be injected, ratio of injected fluid, volume of one or more fluid remaining in a multi-dose medical fluid container after the injection procedure, and various other parameters associated with the contrast media and saline injection fluids may be inputted into and/or displayed on the touch screen of the controller 150 and may be manipulated, viewed, or recorded as required by the user by at least one input or output mechanism, for example, changing parameters by utilizing the touch screen and/or one or more additional controllers in communication with the controller 150. Plunger positions, detection confirmation of disposables, volume of air detected in a patient line, onboard temperatures, medical fluid information, and confirmation of a prime sequence completion may be displayed on the controller 150. Manual or virtual buttons such as fill, purge, prime, and inject buttons and injection start/stop buttons may be included on the controller 150 to adjust the operating parameters of the injector 100. The controller 150 may display or produce audible alerts or other information determined by the fluid control device or the injection system to notify a user of an event, such as low fluid level of a syringe connected to an injector port, the size or type of syringe detected in the injector port, the fluid volume of one or more syringes, the contents of one or more syringes, air detection in one or more syringes, an indication that the syringe has been previously used, an indication whether the syringe's useful shelf-life has expired, a lot number, manufacture date or facility, etc.

In the non-limiting example shown, the controller 150 may be adjustable on the injector housing 125 and may be utilized to operate the fluid delivery system 10 while attached to the injector housing 125. As shown in FIGS. 7 and 8, the display angle of the controller 150 may be adjustable to accommodate different operators having different heights. A bottom or top portion of controller 150 may rotate upwardly or downwardly from the injector housing 125 in a range of 0°-15°. It is contemplated that additional angle ranges may be used in rotating the controller 150. In another example, the controller 150 may be detachable from the injector housing 125 and may be utilized to operate the fluid injection system remotely from other positions in the room and/or, from another room.

The controller 150 may be in communication with the fluid injection system through one or more wired or wireless communication connections, such as through one or more wires, through direct wireless protocols such as Bluetooth, Near Field Communication (NFC) or other radio frequency protocols, and/or through indirect wireless communication, such as through a local Wi-Fi network or secure Internet connection. However, it will be appreciated that various wired and wireless communication mechanisms may be used in accordance with the present disclosure. According to various examples, the controller 150 may include an internal, rechargeable battery, and may be configured to charge or replenish its electrical charge while connected to the injector 100 via one or more ports (not shown) which may provide electrical connections between the controller 150 and injector 100. Additionally or alternatively, the controller 150 may be charged by a standalone charging station or controller, or by connection to an electrical outlet.

Operation of the injector 100 may include use of any combination of the touch screen (either monolithic or detachable), soft-touch keys, and hard-touch keys located on the controller 150, the injector 100, or a wired or wireless local operation station (not shown). In certain examples, one or more images from the scanner may be displayed on the controller 150 for view by the user. For example, test images to help determine the correct orientation or placement of the patient within the scanner, or to locate or confirm that the bolus of contrast has reached the site of interest, may be taken to enhance the imaging process. Further, in certain examples, images may be displayed on the controller 150 to allow the user to confirm that the imaging procedure has been successful, that image clarity is sufficient, and/or to allow quick analysis of the image.

Figure 5:
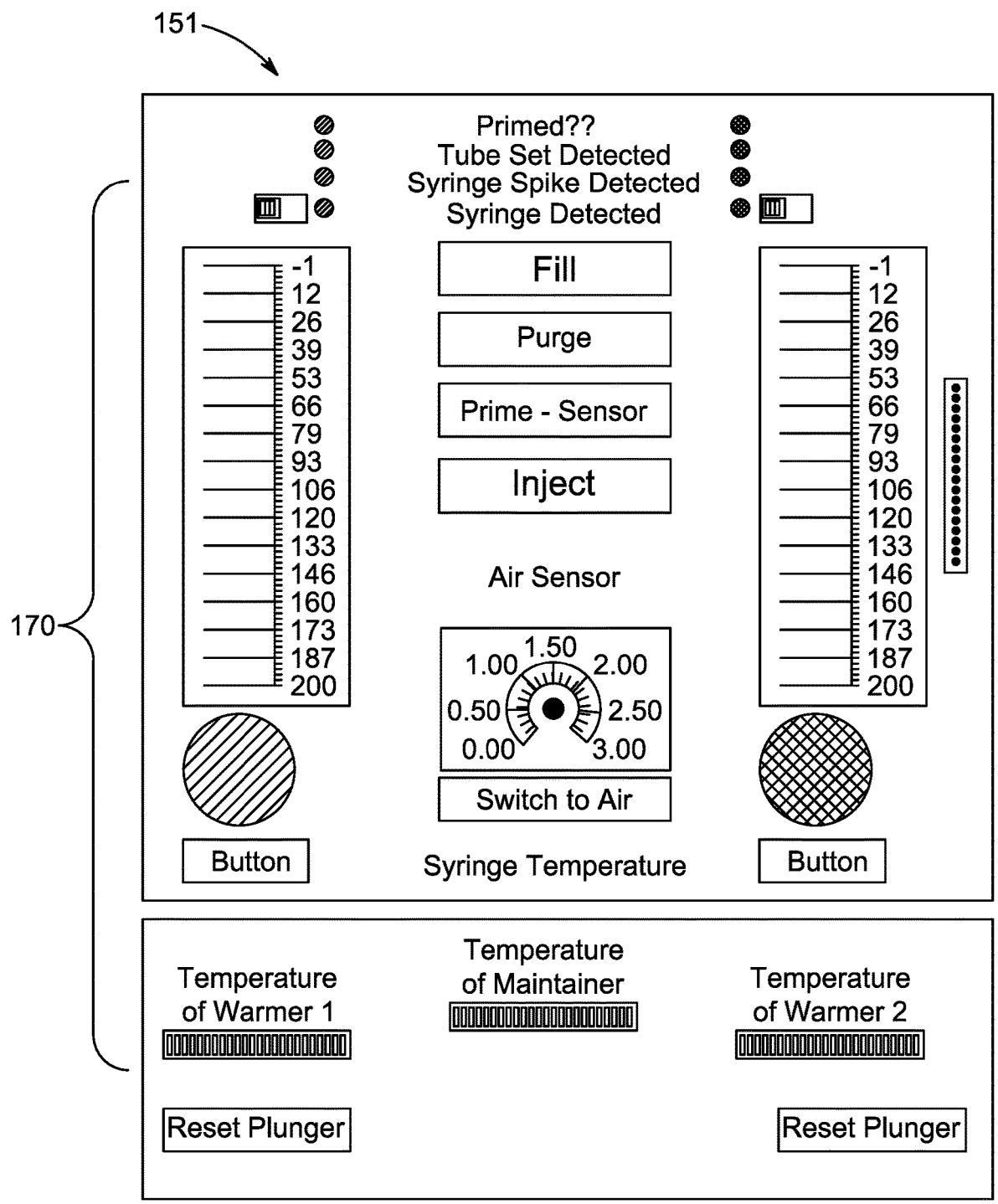
FIG. 5 is an illustration of an exemplary graphical user interface for use with the fluid delivery system of FIG. 1 according to an embodiment.

FIG. 5 shows an example of a graphical user interface (GUI) 151 of a controller 150 in accordance with a non-limiting example of the present disclosure, showing various injection parameters 170 for an injection procedure, displayed on a screen, such as a touch screen. As described herein, the various parameters 170 may be monitored, changed, deleted, and/or inputted by the user before, during, and/or after an injection procedure, for example by touching the appropriate field on the touch screen and entering the appropriate data using an electronic data entry feature, such as a keypad, that appears on the touch screen. In certain examples, some or all of the parameters may be saved and uploaded to a patient records database either wirelessly or by wired connection from the controller 150 or another controller, for example to a hospital information system or network. In configurations, various parameters may be saved and uploaded automatically and/or in response to a user command.

With reference to FIGS. 9A-11B, according to other non-limiting examples, the fluid delivery system 10 of the present disclosure may include one or more stowable stand comprising one or more extendible/retractable poles 200 configured to extend above the injector housing 125 and having at least one hanging feature or hook member such as, for example, one or more pivotable hooks 250 for hanging at least one container such as a multi-dose fluid container in an appropriate position above the injector assembly. According to various examples, the fluid delivery system 10 of the present disclosure may be used for multiple sequential injection procedures, wherein the system includes a multi-patient use portion and a single-patient use portion. In these examples, the at least one syringe may be a multi-use syringe that may be repeatedly refilled with the appropriate medical fluid between a series of fluid injection procedures from at least one multi-dose fluid container, such as a saline bag or container, a bulk contrast bottle, or other appropriate bulk medical container.

For ease of use and convenience, the at least one multi-dose fluid container may be suspended in an inverted position above the housing 125 from a hanging feature 250 such as a hook, tray, or other protrusion, while filling or refilling the at least one syringe or additionally during the injection procedure where the fluid container is not in fluid communication with the at least one syringe. Thus, the multi-dose fluid containers may be readily available after an injection procedure to refill the at least one syringe, fill one or more new syringes (in a single-dose protocol), and/or prepare the fluid injection system for a subsequent injection procedure.

Figure 9A:
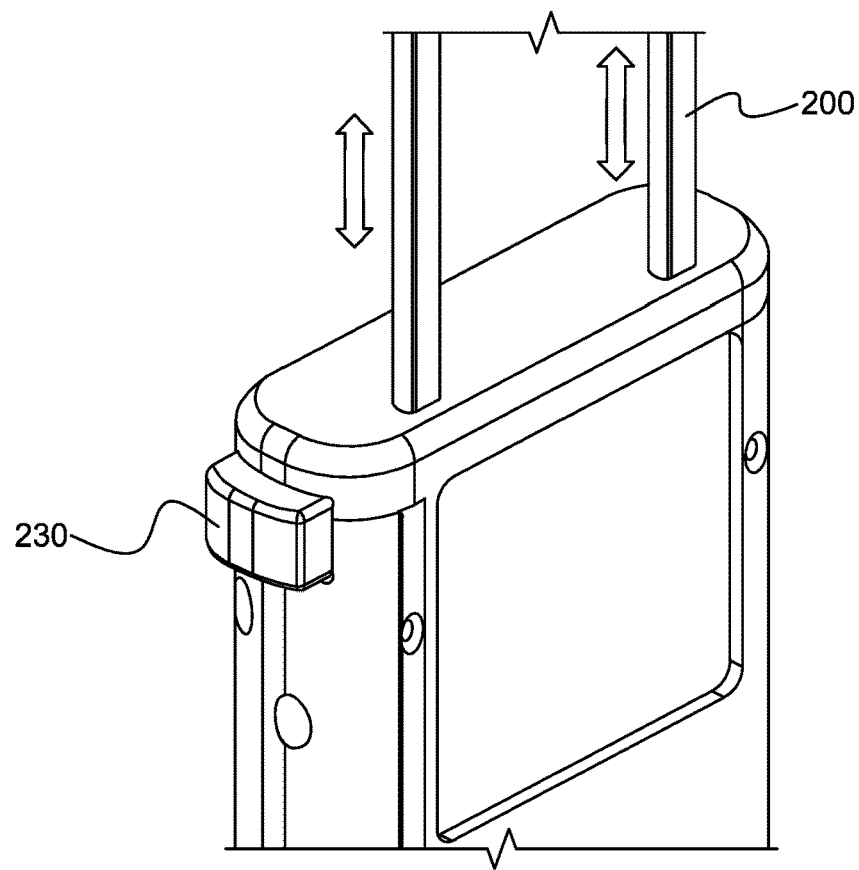
FIG. 9A is an isolated view of a stowable stand in the fluid delivery system of FIG. 1 according to an embodiment.
Figure 9B:
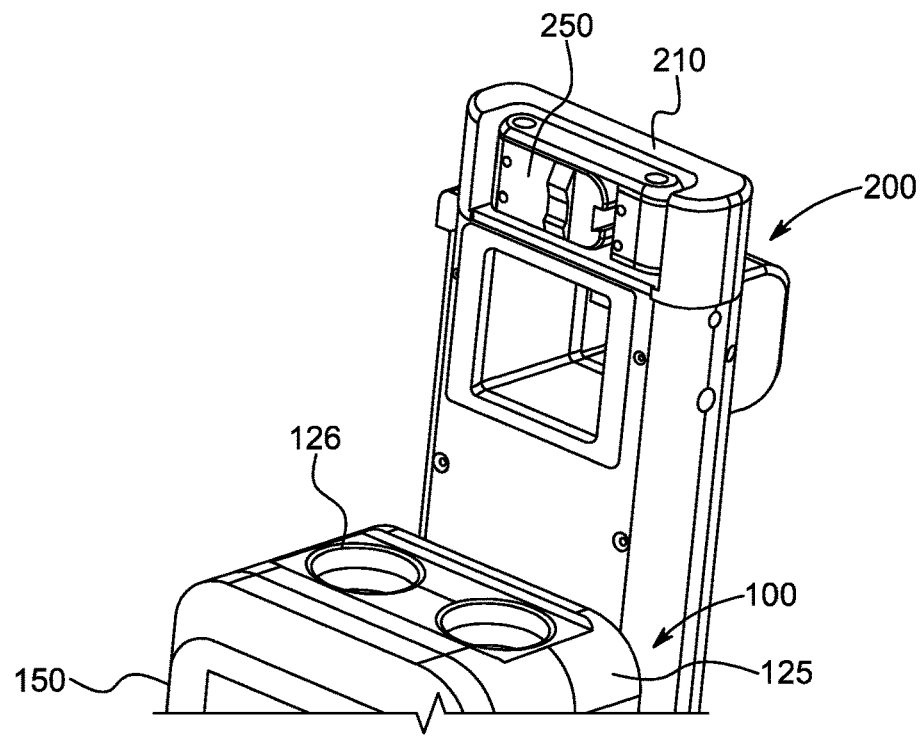
FIG. 9B is an isolated view of the stowable stand of FIG. 9A according to an embodiment in a stowed position.
Figure 9C:
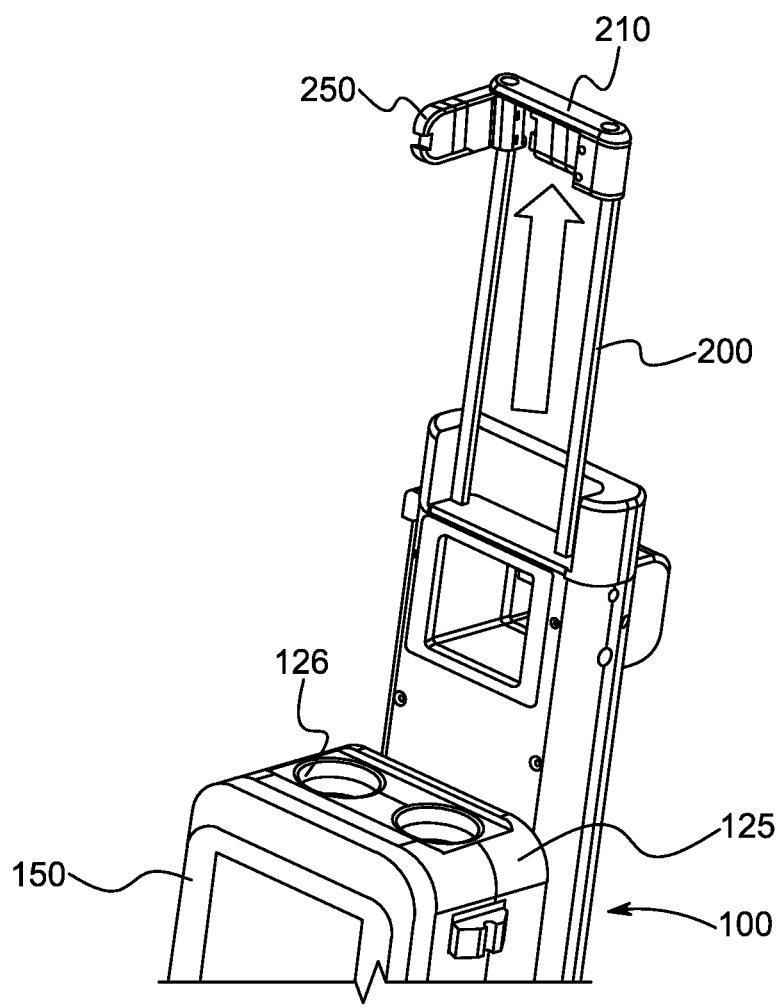
FIG. 9C is an isolated view showing the stowable stand of FIG. 9A according to an embodiment in an extended position.

FIGS. 9A-9C illustrate one embodiment of an injector 100 having a stowable stand comprising a retractable pole 200 according to a non-limiting example of the fluid injection system of the present disclosure. Referring to FIG. 9C, the retractable pole 200 is shown in a retracted or stowed position for storage and to minimize the height of the injector 100 as well as eliminate the requirement for a separate rollable IV pole to hang the one or more medical fluid containers. The retractable pole 200 includes a handle 210 or other gripping surface configured for gripping by a user and to facilitate the extension and/or retraction of the pole 200 upwards above the support portion 118. Alternatively, the retractable stand may be spring loaded, motorized, or hydraulically operated to move between the stowed and the deployed positions. In certain examples, retractable pole 200 may be held or locked in a specific position that may be disengaged by pressing button 230 before or concurrently with moving handle 210. In other embodiments where retractable stand 220 is motorized or hydraulic, a button on the GUI of the controller may be used to extend and/or retract pole.

Figure 10A:
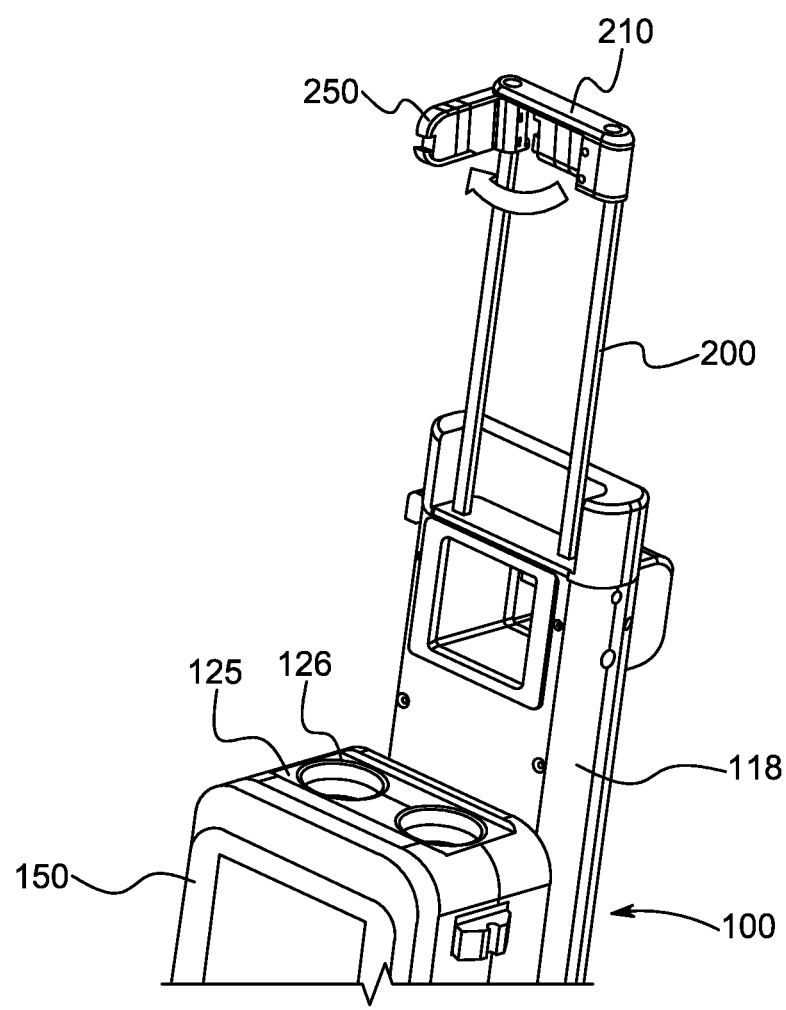
FIG. 10A is an isolated view of the stowable stand of FIG. 9A according to an embodiment having a hook member being rotated into an extended position.
Figure 10B:
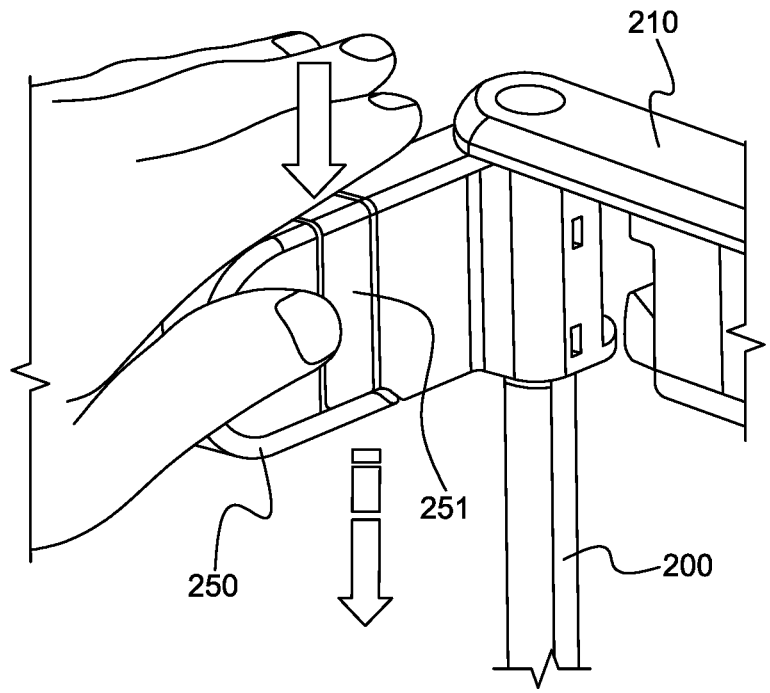
FIG. 10B is an isolated view of the hook member of FIG. 10A.
Figure 10C:
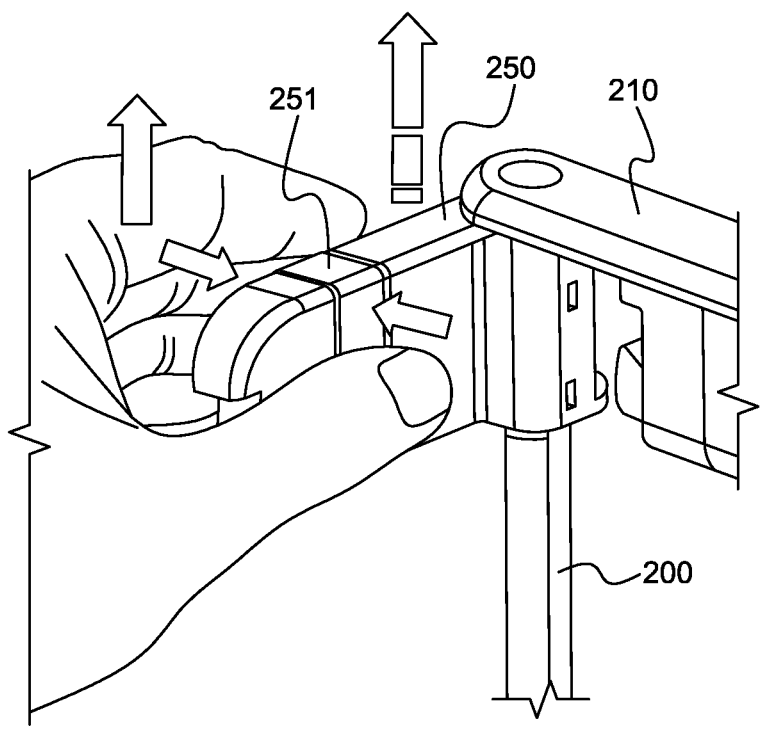
FIG. 10C is an isolated view of the hook member of FIG. 10A.

FIG. 9C illustrates an embodiment of injector 100 with the retractable pole 200 in an extended or deployed position. In the non-limiting example shown, the retractable pole 200 is provided with a plurality of pivotable hooks 250 or hanging features with at least one hook member 250 being pivotable from a retracted position, wherein hook 250 is substantially contained within or aligned parallel with the handle 210, to a deployed position wherein the at least a portion of hook 250 rotates and extends perpendicular to the handle 210 either over the at least one syringe or extending behind the injector. With reference to FIGS. 10A-10C, after the hooks 250 have rotated perpendicular to the handle 210, the height of the hooks 250 on the poles 200 may be adjusted independently depending on the desired height for holding the specific medical fluid container. Each hook 250 may include a button or release catch 251 that may be activated by an operator to release the hook member and allow the operator to slide the hooks 250 downwardly and/or upwardly on the poles 200 until the desired height is reached. As will be described below, the hooks 250 may be moved to either clamp down on or hold a bulk container that is used to fill one or more of the syringes in the injector 100 (see for example, FIG. 11A) or may be moved to bring the hook 250 and a multi-dose bulk fluid container (252, 254 and 256) to the appropriate position relative to the one or more syringes in the injector 100 to allow connection with and fluid communication between the one or more bulk container and the respective one or more syringes (for example, FIGS. 11B, 12A, 12B and 13A). The operator may also activate the button 251 to move the hooks 250 upwardly away from the syringes in the injector 100.

Figure 11A:
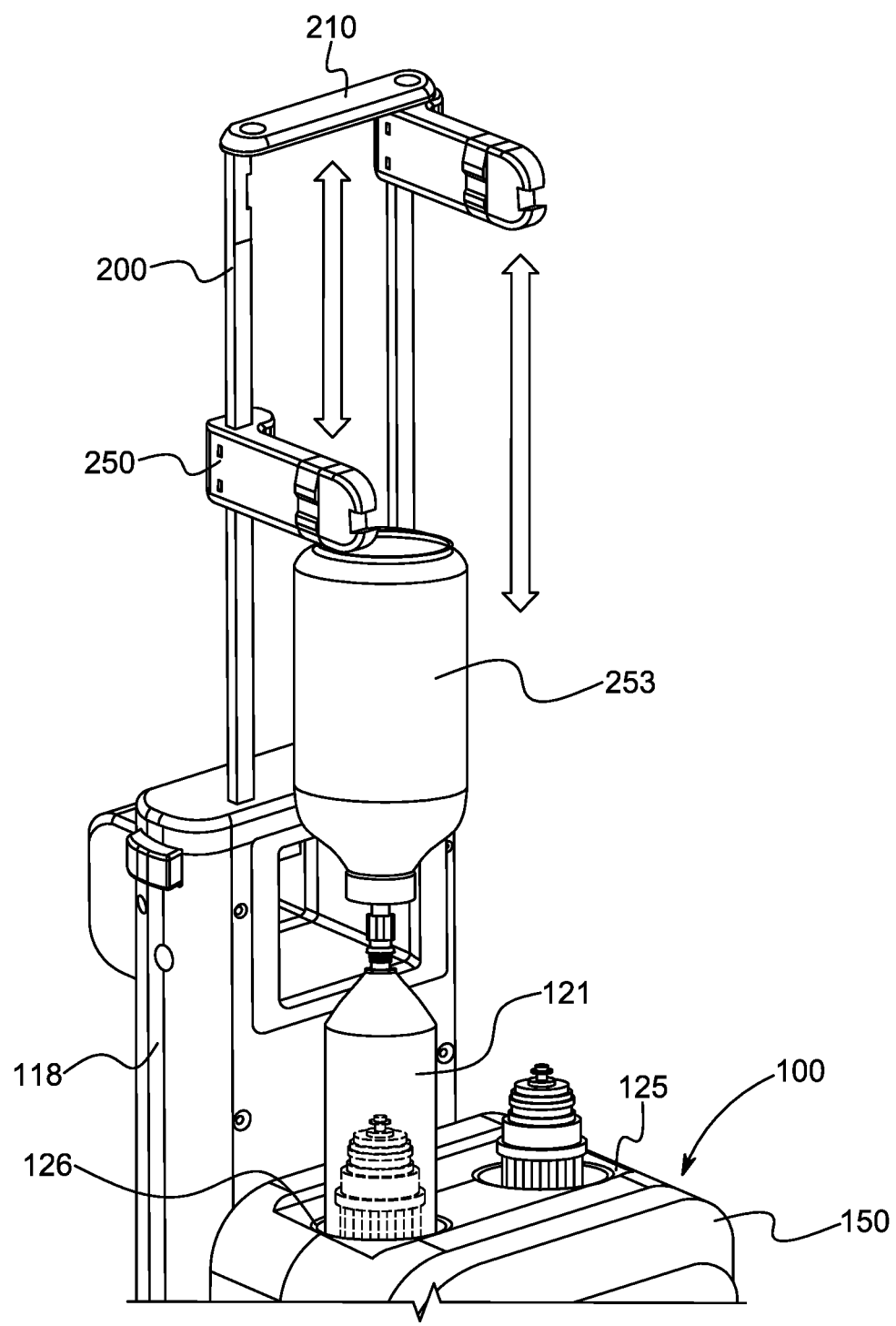
FIG. 11A is an isolated view showing the stowable stand of FIG. 9A according to an embodiment securing a bottle to the fluid delivery system of FIG. 1 using a hook member.
Figure 11B:
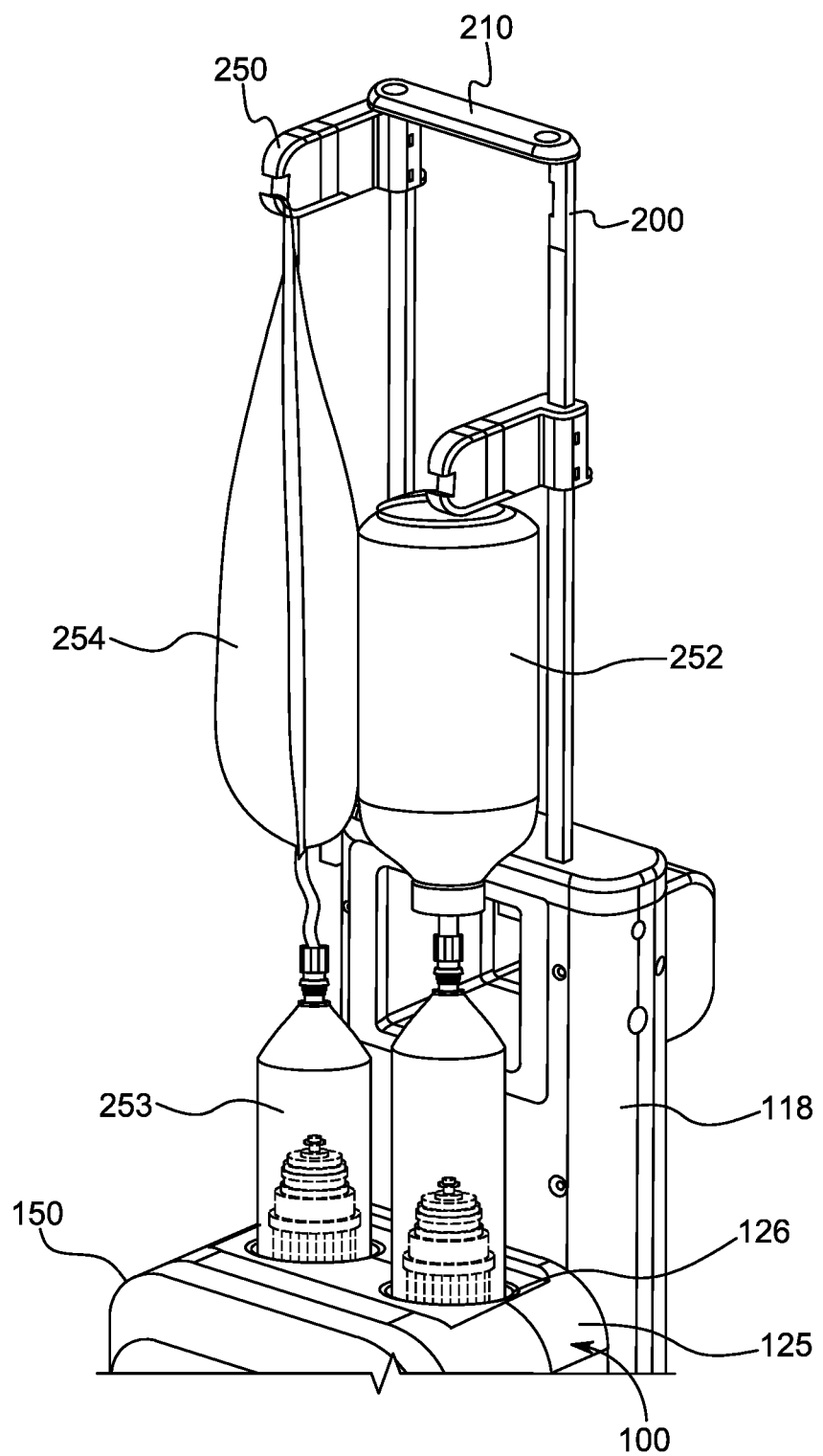
FIG. 11B is an isolated view of the stowable stand of FIG. 9A according to an embodiment holding a fluid bottle and a fluid bag.

FIG. 11A shows an example of the retractable pole 200 of the injector 100 in the fully deployed position where the at least one hook 250 is deployed vertically over at least one syringe 253. In this position, shown in FIG. 11A, one or more multi-dose bottles 252 may be connected to a syringe 253 held within the injector housing 125. The hooks 250 may be moved downwardly on the poles 200 to bring the hooks 250 into contact with a bottom surface of the bottles 252 to stabilize the bottles 252 when connected to the syringes 253. In one example, the bottles 252 may hold a bulk amount of a contrast medium. In another example, shown in FIG. 11B, one or more multi-dose fluid bags 254 may be hung from the pivotable hooks 250 in an inverted position over the at least one syringe 253 and attached to the fluid port of the syringe 253 by a fluid path (see, for example, FIG. 12B) to allow fluid communication and flow of medical fluid from the multi-dose fluid container 252 or multi-dose fluid bag 254 to the at least one syringe 253. In one example, the multi-dose fluid bag 254 may hold saline. As shown in one example in FIG. 11B, a multi-dose fluid bottle 252 may be provided on the injector 100 to provide fluid to a first syringe 253 and a multi-dose fluid bag 254 may also be provided to supply fluid to a second syringe 253.

Figure 12A:
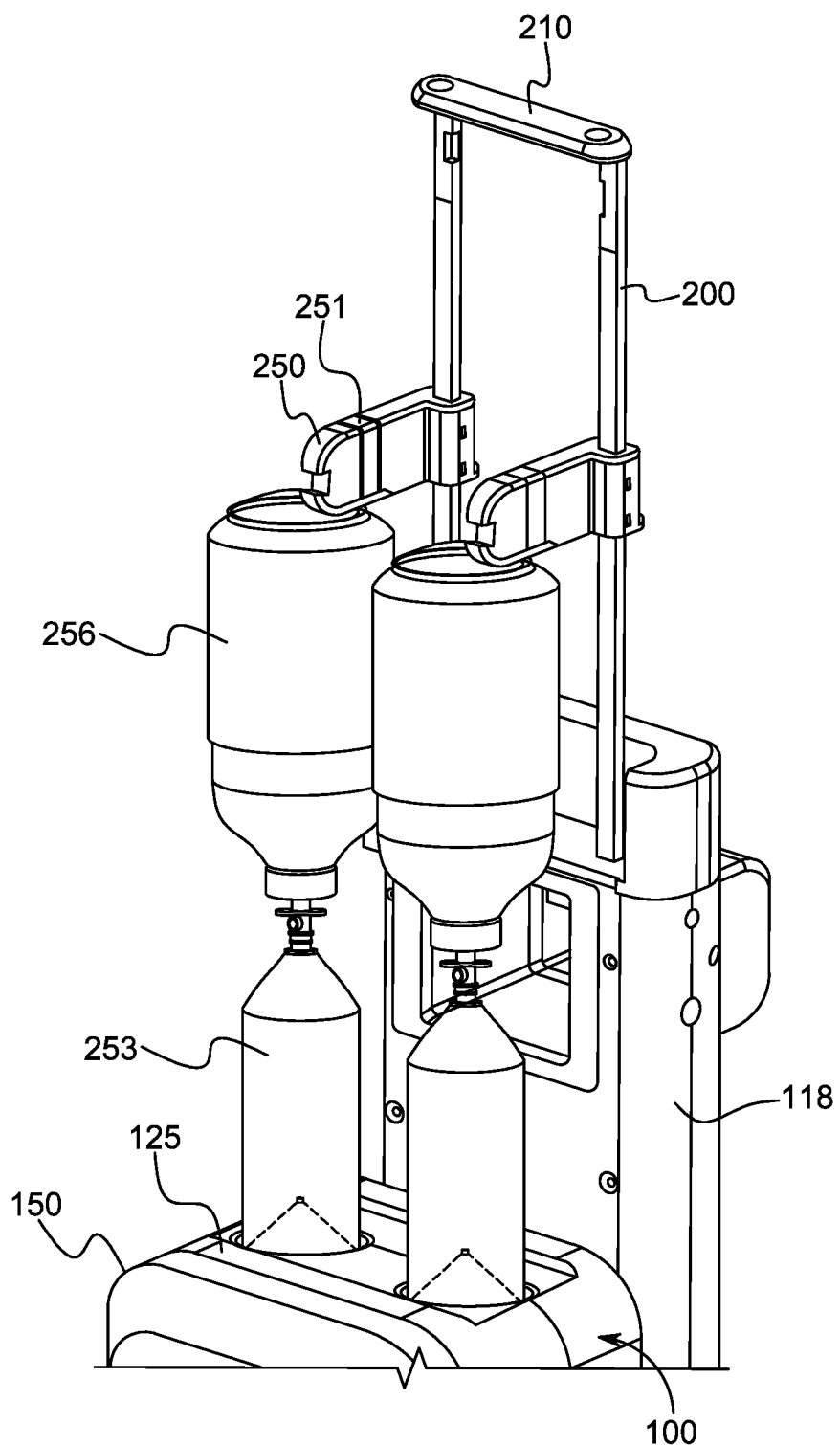
FIG. 12A is an isolated view showing the stowable stand of FIG. 9A according to an embodiment holding multi-dose fluid bottles.
Figure 12B:
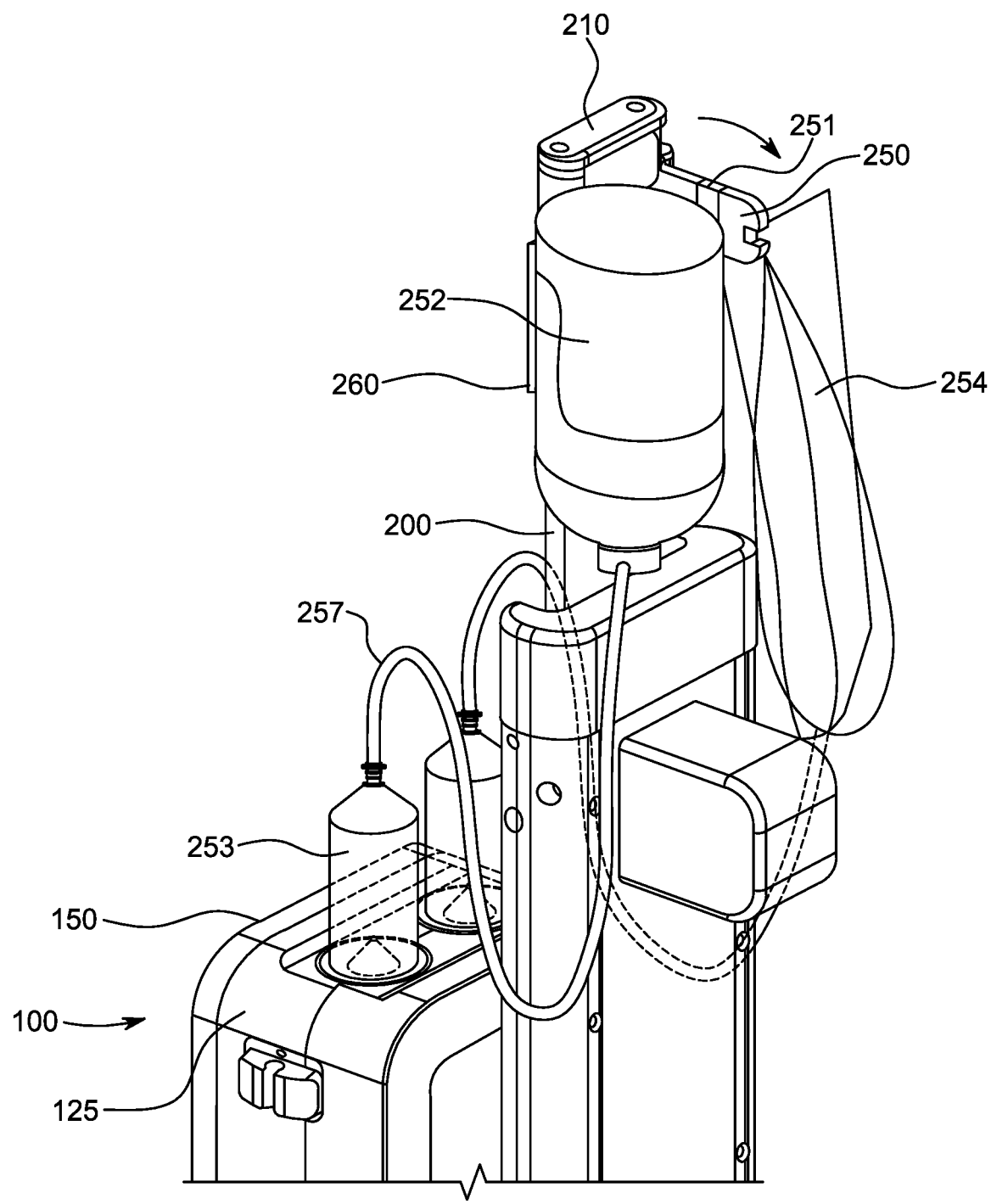
FIG. 12B is an isolated view showing the stowable stand of FIG. 9A according to an embodiment holding a multi-dose fluid bottle and a multi-dose fluid bag.

With reference to a non-limiting example in FIGS. 12A and 12B, the injector 100 may be used with any combination of single-dose fluid containers (FIG. 12A) for a single patient and/or with multi-dose fluid containers (FIG. 12B) for a single patient. In one example, shown in FIG. 12A, at least one syringe 253 may be filled with fluid from a single-dose fluid container 256 in fluid communication with the at least one syringe 253 for example by a spike or other appropriate fluid path. After the syringe 253 has been filled with fluid from the single-dose fluid container 256, the single-dose fluid container 256 may be removed from the injector 100 and replaced with another single-dose fluid container. The hooks 250 may stabilize the single-dose fluid container 256 on the syringe 253 or may hold the single-dose fluid container 256 at the appropriate height above the syringe 253. In another example, shown in FIG. 12B, at least one syringe 253 may be filled with fluid from a multi-dose bulk fluid container 252 and/or multi-dose hulk fluid bag 254. The syringe 253 may be connected to and in fluid communication with a multi-dose fluid container 252 or bag 254 via a transfer set 257 that is connected at one end to the syringe 253 and at another end to the multi-dose fluid container 252, for example by a spike, to transfer fluid therebetween. The multi-dose fluid container 252 may be a bottle (which may contain a bulk amount of contrast medium or other medical fluid) or a bag (which may include saline). In another example, one syringe 253 may be connected to a multi-dose fluid bottle 252 and a second syringe 253 may be connected to a multi-dose fluid bag 254. The multi-dose fluid bag 254 may hang from a hook 250 supported on the pole 200. In various embodiments, the multi-dose fluid bottle 252 may include an insulating or heated sleeve 260 that is received on the pole 200 to maintain the multi-dose fluid bottle 252 at a desired height relative to the syringe 253 and to maintain a fluid temperature of the fluid in the multi-dose fluid bottle 252, for example a contrast medium in the multi-dose fluid bottle 252. The multi-dose fluid bottle 252 may be removably provided within the insulating or heated sleeve 260. According to another example, one syringe 253 may be connected to a single-dose fluid bottle 256 and a second syringe 253 may be connected to a multi-dose fluid bag 254.

Figure 13A:
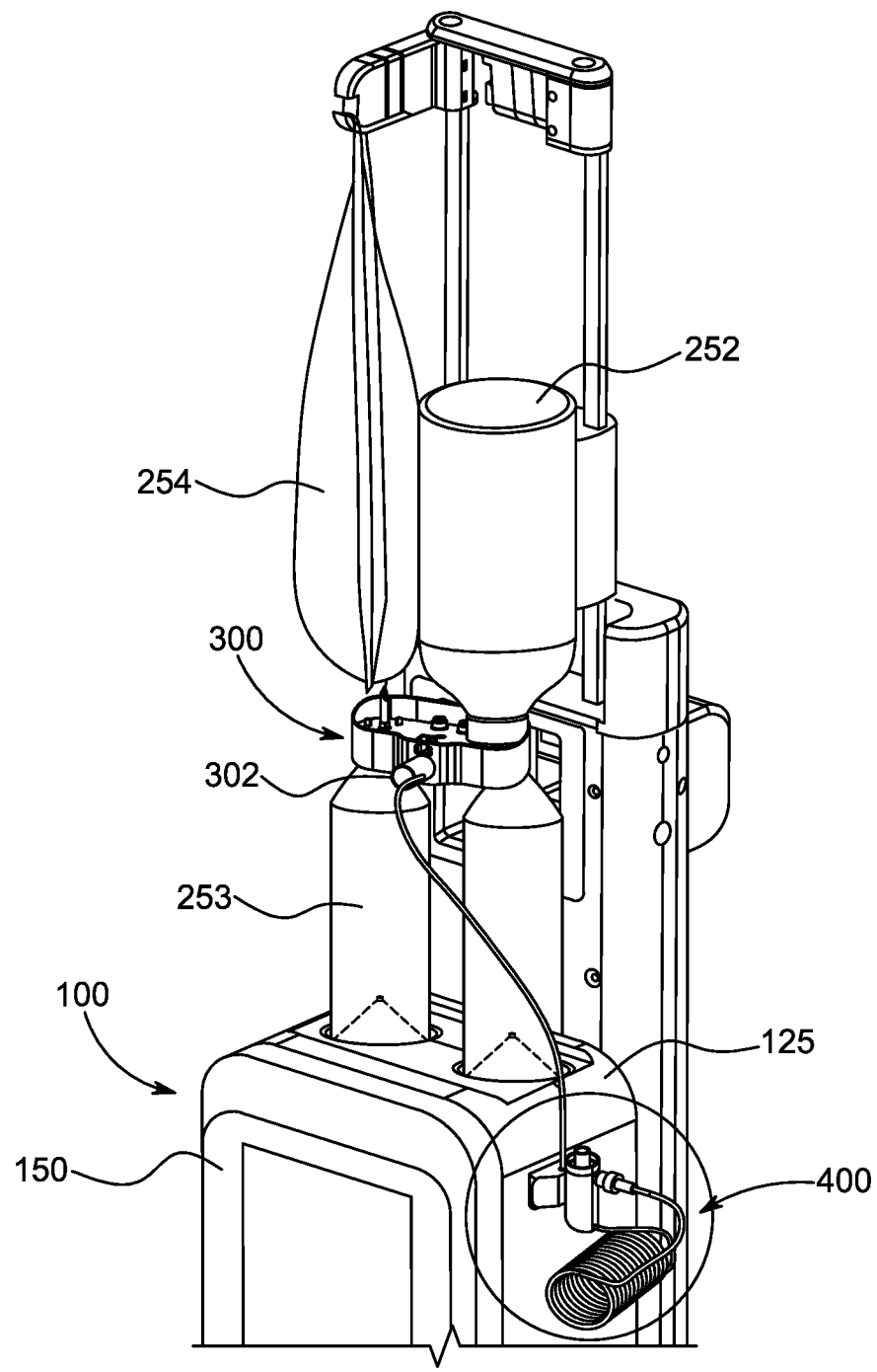
FIG. 13A is an isolated view showing multi-dose fluid containers connected to a manifold assembly according to an embodiment.
Figure 13B:
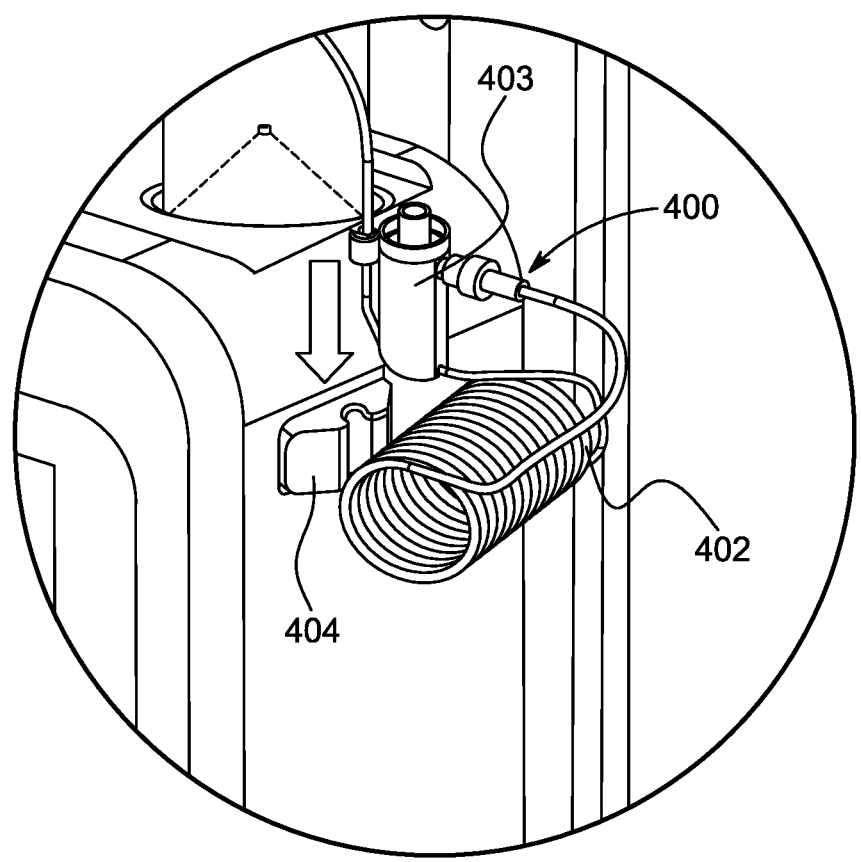
FIG. 13B is an exploded view of an air detector coupling used with the manifold assembly of FIG. 13A according to an embodiment.

With reference to FIGS. 13A and 13B, an embodiment of fluid injection system 10 including injector 100 may be used to provide fluid to multiple patients in a series of injection procedures, for example two or more injection procedures spaced over a period of time. As described above, multi-dose fluid containers 252, 254 may be connected to one or more syringes 253 engaged with the injector housing 125 to repeatedly fill the one or more syringes 253 with fluid from the multi-dose fluid containers 252, 254 over the course of a plurality of injection procedures. In one example, a multi-dose fluid bottle 252 may be connected to a first syringe 253 and a multi-dose fluid bag 254 may be connected to a second syringe 253, in one example, the multi-dose fluid bottle 252 and multi-dose fluid bag 254 may be connected to the syringes 253 via a multi-patient use manifold assembly 300 that may be utilized over a plurality of injection procedures (described in greater detail herein). The manifold assembly 300 and one or more syringes 253 connected thereto may be configured to supply fluid from the multi-dose fluid bottle 252 and/or multi-dose fluid bag 254 to multiple patients over the course of a plurality of injection procedures. An outlet 302 defined in the manifold 300 directs fluid out of the manifold 300 to the multiple patients via connection lines, such as a single-patient disposable fluid path set (single-use disposable sets or "SUDS") having a first end for releasable connection with the manifold and a second end configured for connection to a needle, catheter or other connection feature connected to a patient to provide fluid communication between the manifold and the vasculature of the patient (not shown). Suitable single-use disposable sets are described in detail in International Application Publication No. WO 2015/106107, which disclosure is incorporated in its entirety by this reference. The single-patient disposable fluid path set may include appropriate connector assemblies and one, two or more check valves to prevent fluid backflow of potentially contaminated fluid from the single-patient disposable fluid path set into the multi-patient use manifold assembly 300.

As shown in FIG. 13B, an air detector coupling 400 may be provided on the injector 100 according to one example to provide a line presence detector that detects a line coupling to the manifold 300 and to initiate an auto prime routine. The auto prime routine assists in removing any significant amounts of air provided in the patient lines, such as the SUDS. The air detector coupling 400 may include a single-patient use tubing set or line coupling (SUDS) 402. One end of the SUDS coupling 402 may be connected to the manifold assembly 300 and an opposing end of the SUDS coupling 402 may be connected to an excess fluid container 403 or held in position to expel fluid into an appropriate container. An additional portion of the SUDS coupling 402 may be held on the excess fluid container 403. The excess fluid container 403 may be held on the injector housing 125 by sliding into a coupling interface 404 extending from the injector housing 125. In one example, the coupling interface 404 may include an air detector, such as an ultrasonic air detector, to detect air that may be present in the SUDS coupling 402. During a priming operation, the air detector may determine when all or substantially all excess air has been expelled from the SUDS coupling 402, and indicate that the system is primed and ready for an injection procedure.

The SUDS coupling 402 may be primed before attachment of the SUDS coupling 402 to the vasculature system of the patient. Upon insertion of the SUDS coupling 402 into the coupling interface 404, an auto prime process may be initiated. Fluid may be pushed through the SUDS coupling 402 from the manifold assembly 300, thereby pushing any air present in the SUDS coupling 402 into the excess fluid container 403. The air stored in the excess fluid container 403 may then be vented to atmosphere. As the air is pushed through the SUDS coupling 402, any excess fluid in the SUDS coupling 402 may also be pushed into the excess fluid container 403. During the prime process of the SUDS coupling 402, the coupling interface 404 may monitor and detect the presence of any air in the SUDS coupling 402. Once the coupling interface 404 has determined that there is no longer air present in the SUDS coupling 402, the SUDS coupling 402 may be removed from the excess fluid container 403 and placed in fluid connection with the vasculature of a patient.

The air detector coupling 400 monitors air and fluid passing through the SUDS coupling 402 during the auto prime routine. Once a constant fluid flow is detected to be passing through the SUDS coupling 402, the system delivers sufficient further volume of fluid to ensure complete fluid fill of the coiled section of the SUDS coupling 402. The excess fluid container 403 may capture any excess fluid from the initial air/fluid mix delivery or any manufacturing tolerances and accuracy allowances in the coiled section of the SUDS coupling 402. During the injection sequence, air and fluid is constantly monitored as it passes through the air detector coupling 400. The system halts injections at a point when the volume of air passing through the air detector coupling 400 reaches a pre-determined safety level to protect against injecting the patient with dangerous volumes of air or air/fluid mix. The air detector coupling 400 may be located at the distal end of the SUDS coupling 402 (e.g., further from the patient) to allow maximum time for the system to react to the air detector coupling 400 and stop the injection before the air reaches the patient. The amount of air injected is recorded by the system and may be included in a procedure report. Accurate air detection can require constant surface contact and a constant contact surface area between the SUDS coupling 402 and the coupling interface 404 of the air detector coupling 400. The SUDS coupling may be inserted into the detection region of the air detector by pressing the tubing into the detection region. If the tubing is not fully inserted into the detector, for example by applying insufficient force to insert the tubing into the air detector, inaccurate air detection may result due to lack of full surface contact and reading of air present between the tubing and the detector surface. In certain examples, the present system slides the tubing of the SUDS coupling 402 into the coupling interface 404 of the air detector coupling 400, for example from top to bottom, resulting in improved and consistent contact between the tubing surface of the SUDS coupling 402 and the coupling interface 404 of the air detector coupling 400, thus ensuring that air detection detects air primarily within the tubing.

Figure 14A:
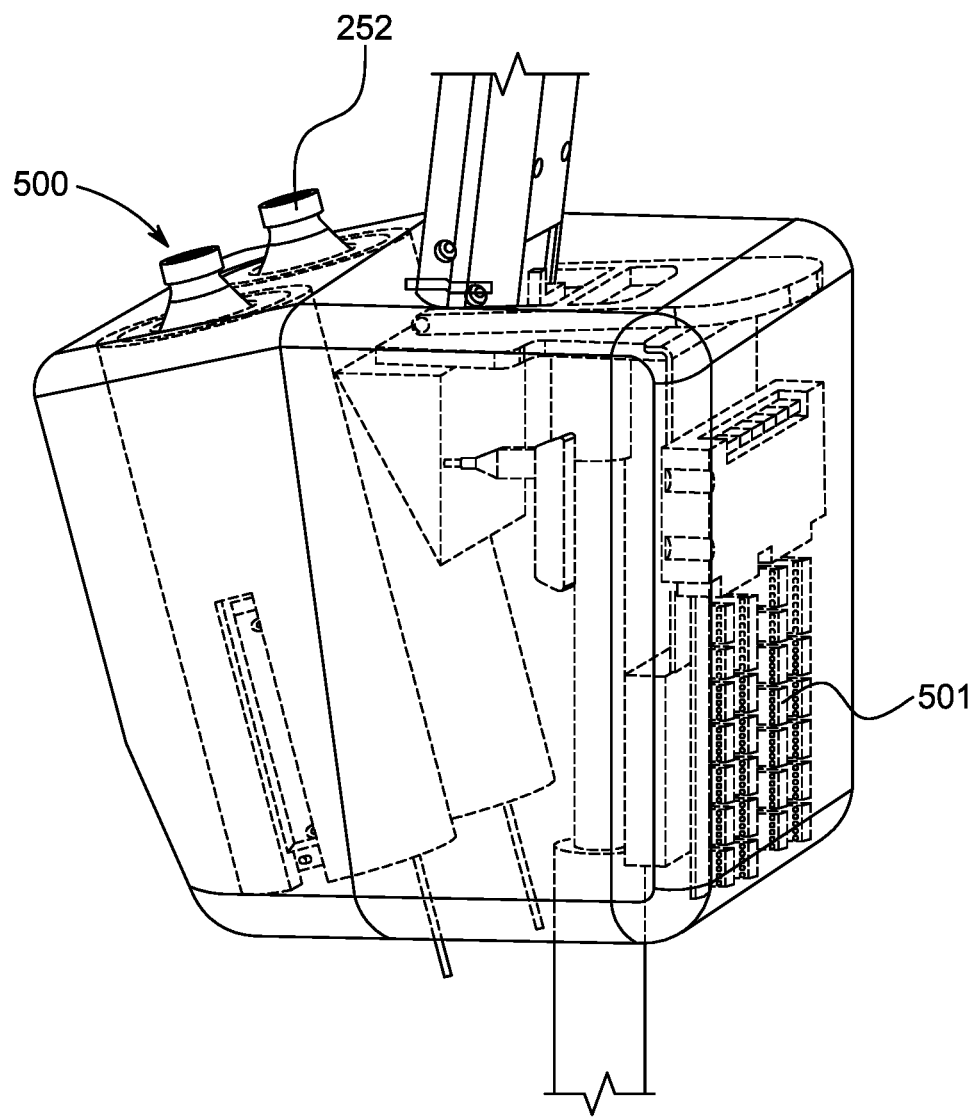
FIG. 14A is an isolated view of a fluid warmer according to an embodiment of the fluid delivery system of FIG. 1.
Figure 14B:
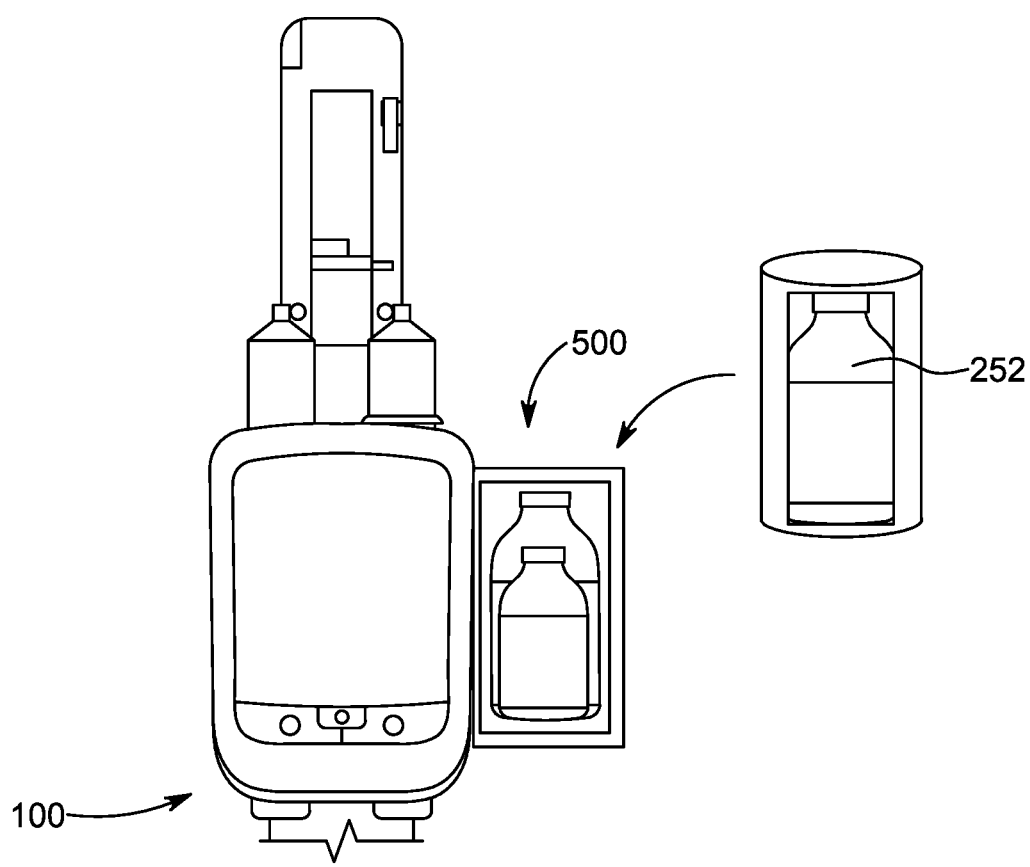
FIG. 14B is a schematic view of a fluid warmer according to another embodiment of the fluid delivery system of FIG. 1.

With reference to FIG. 14A, according to certain examples the fluid delivery system 10 may also include a fluid warmer 500 to warm the multi-dose and/or single-dose medical fluid container, 252 or 256 respectively, and medical fluid contained therein. Certain medical fluids, such as certain contrast fluids, may have high viscosities at room temperature, which may affect the fluid flow and injection pressure during an injection procedure. The viscosity of the medical fluid may be reduced by warming the fluid to above room temperature, such as a temperature at or near body temperature. In one example, the fluid warmer 500 may be positioned on the fluid delivery system 10 below the injector housing 125 and may be supported on the lower support portion 120. The fluid warmer 500 may be used by a technician to warm at least one multi-dose fluid bottle 252 or at least one single-dose fluid bottle 256 before transferring the fluid in the multi-dose fluid bottle 252 into a syringe 253 as described herein. The multi-dose fluid bottle 252 may be inserted into and removed from the fluid warmer 500 via openings defined in the fluid warmer 500. In one example, the multi-dose fluid bottle 252 may hold a contrast medium that can be warmed with the fluid warmer 500. In one example, the multi-dose fluid bottles 252 may be held in a bottle storage tray (not shown) provided in the fluid warmer 500. In one example, the fluid warmer 500 is configured to warm two or more multi-dose fluid bottles 252. A technician may remove a warmed multi-dose fluid bottle 252 from the fluid warmer 500 and use for loading syringes for an injection procedure and may replace the warmed multi-dose fluid bottle 252 with a second multi-dose fluid bottle added to the fluid warmer 500 to begin warming the second multi-dose fluid bottle. In one example shown in FIG. 14B, the fluid warmer 500 may be cylindrical to minimize an air cavity within the fluid warmer 500. The fluid warmer 500 may be configured to accommodate different sizes of bottles. Demonstrator electronics 501 may be provided inside of the fluid warmer 500 to control heating elements (not shown) used to warm the multi-dose fluid bottles 252. The demonstrator electronics 501 may include at least one infrared temperature sensor to record the temperature of the bottles in the fluid warmer 500. The demonstrator electronics 501 may be accessed by a technician by removing the rear access cover 122 from the fluid delivery system 10. In one example, the fluid warmer 500 may be configured to warm fluid in multi-dose fluid bottles 252 from room temperature to at/near a patient's body temperature. In another example, the fluid warmer 500 may be configured to warm fluid in multi-dose fluid bottles 252 to a temperature in the range of 20° C.-37° C. It is also contemplated for certain examples that the fluid may be initially warmed to a higher temperature, such as a temperature in the range of 20° C. to at least 41° C., and allowed to cool to the desired temperature prior to being utilized in an injection procedure or may cool to a desired temperature within the syringe or while flowing through the one or more tubing sets. In various embodiments, a technician may control the temperature in the fluid warmer 500. The fluid warmer 500 and/or the controller GUI may include a temperature display to show the current temperature in the fluid warmer 500 and/or the final heated temperature in the fluid warmer 500. In certain embodiments, the controller may prevent an injection procedure when a measured temperature of the fluid is outside a desired range, such as above body temperature. The fluid warmer 500 may also log the temperatures provided in the fluid warmer 500 and may use this information with the rest of the fluid delivery system 10. In one example, the fluid warmer 500 may be configured to maintain a predetermined temperature to ensure the bottles are heated at the desired temperature. In one example, the fluid warmer 500 may use microwave or infra-red heating to provide the required energy to heat the bottles. In another example, the fluid warmer 500 may utilize resistive heating to heat the bottles. Fan-forced air may be used to improve the heating in the fluid warmer 500, which may be used in conjunction with a downstream heating system. The fluid warmer 500 may also assist in sterilizing or maintaining sterility of the multi-dose fluid bottles 252 before being used with the injector 100. Warming the fluid in the multi-dose fluid bottles 252 also makes the injection of the fluid into a patient more comfortable for the patient. Warming the fluid in the multi-dose fluid bottles 252 also allows for higher flow rates during injection because the viscosity of the fluid is reduced by higher temperatures generated by the fluid warmer 500. In one example, the fluid in the multi-dose fluid bottle 252 may be warmed to approximately the patient's body temperature so, upon injection of the fluid into the patient, the fluid is at or near the same temperature as the patient's body. In one example, the fluid warmer 500 may be manually operated by the technician and activated/deactivated as needed by the technician. Alternatively, the fluid warmer 500 may be automatically activated upon insertion of a multi-dose fluid bottle 252 into the fluid warmer 500 and automatically deactivated upon removal of the multi-dose fluid bottle 252 from the fluid warmer 500. The fluid warmer 500 may be deactivated when the bottle or bottles are empty. The fluid warmer 500 may also be configured to receive a multi-dose fluid bag 254 or a single-dose bottle or bag. Further, the system may record the details of the heated bottles 252 by a barcode scanner (not shown), such as the final temperature and/or duration of heating of the bottles. This information may be stored in records for compliance requirements. The temperature at injection may also be recorded by a sensor (not shown) at the syringe and may be included in a procedure report. Suitable non-limiting structures and direct methods for measuring fluid temperature at the syringe may be found for example in U.S. Provisional Application No. 62/005,346. Temperature sensing of the fluid within the syringe may also be performed using indirect methods, such as infrared readings.

Figure 15:
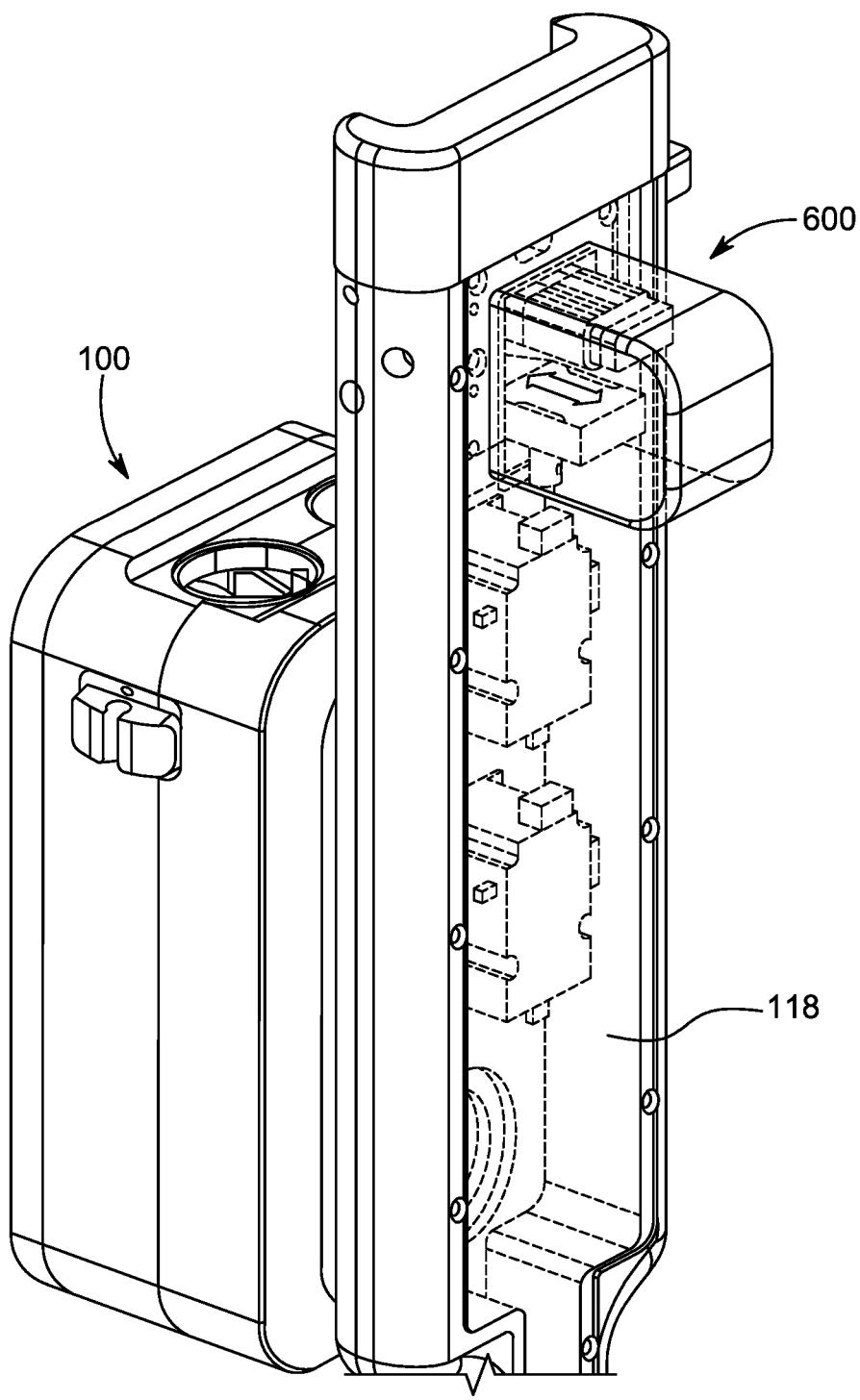
FIG. 15 is an isolated view of an embodiment of a recognition system provided on the fluid delivery system of FIG. 1 according to an embodiment.
Figure 16:
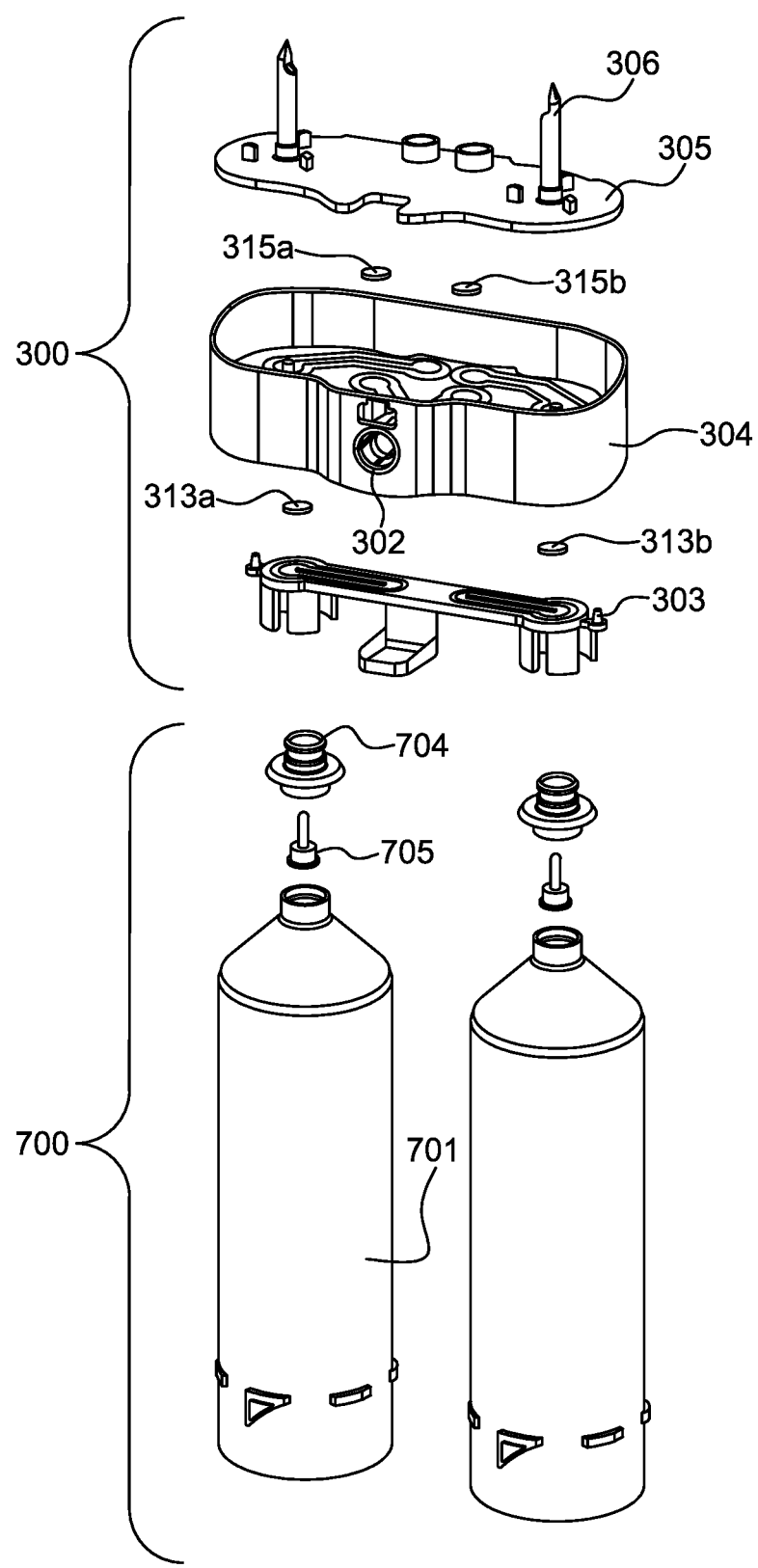
FIG. 16 is an exploded view of the manifold assembly of FIG. 13A according to an embodiment.

With reference to FIG. 15, a recognition system 600 may also be provided on the injector 100. The recognition system 600 may be removably provided on the support portion 118 of the injector 100. In one example, the recognition system 600 may be positioned behind the syringes 253 when the syringes 253 are being filled with fluid from a single- or multi-dose fluid bottle or bag. The recognition system 600 may be configured to identify various features and/or properties of the fluid in each syringe 253, as well as the type of disposable syringe. Based on the information identified by the recognition system 600, the injector 100 may adjust its operating parameters to achieve desired filling and injection parameters. Examples of suitable recognition systems are described in U.S. Application Publication No. 2017/0056603, incorporated herein by this reference.

With reference to FIGS. 16-18C, embodiments of manifold assemblies 300 and syringe assemblies 700 according to various examples are described. The manifold assembly 300 and syringe assembly 700 may be configured for use in a multi-patient, multi-dose injector 100. The manifold assembly 300 may be configured to fluidly connect at least one multi-dose bottle or bag to at least one syringe assembly 700 to allow filling of the at least one syringe in the syringe assembly 700 with a medical fluid from the at least one multi-dose bottle or bag and allow delivery of the medical fluid from the at least one syringe to the patient via a single-patient use tubing set (SUDS, not shown) connected to an outlet 302 of the manifold assembly 300 at a first end and the patient at a second end. According to certain embodiments, the manifold assembly 300 may include a lower body member 303, a middle body member 304, and an upper body member 305. The lower body member 303 is configured to fit within or attached to a lower portion of the middle body member 304. The upper body member 305 is configured to fit within or attach to an upper portion of the middle body member 304. As shown in FIG. 17A, the upper body member 305 includes at least one fluid conducting element, such as a spike member 306, used to pierce or connect to a septum or cap on a fluid bottle or bag. It is to be understood that fluid conducting elements other than a spike member can also be used, such as a fluid connector. The at least one spike member 306 creates fluid communication between the fluid bottle or bag and the manifold assembly 300. The at least one spike member 306 may have a pointed end used to pierce the septum or cap on the fluid bottle and at least one fluid path to allow fluid communication between the fluid bottle or bag and the manifold assembly 300. In one example the at least one spike member 306 may further include a second fluid path to allow air or other gas to pass into the fluid bottle or bag to equalize the pressure in the interior of the fluid bottle or bag.

Figure 17A:
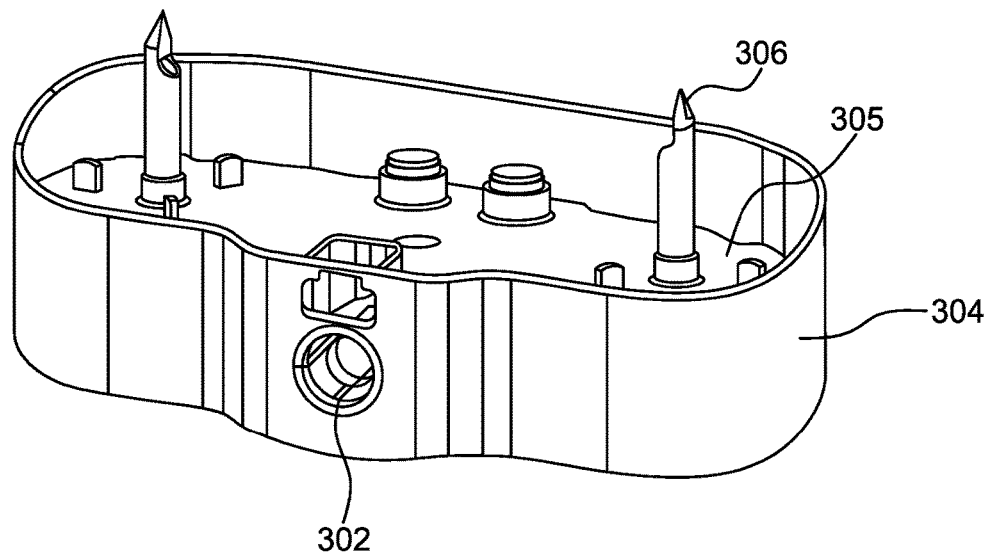
FIG. 17A is a front perspective view of the manifold assembly of FIG. 16 according to an embodiment.
Figure 17B:
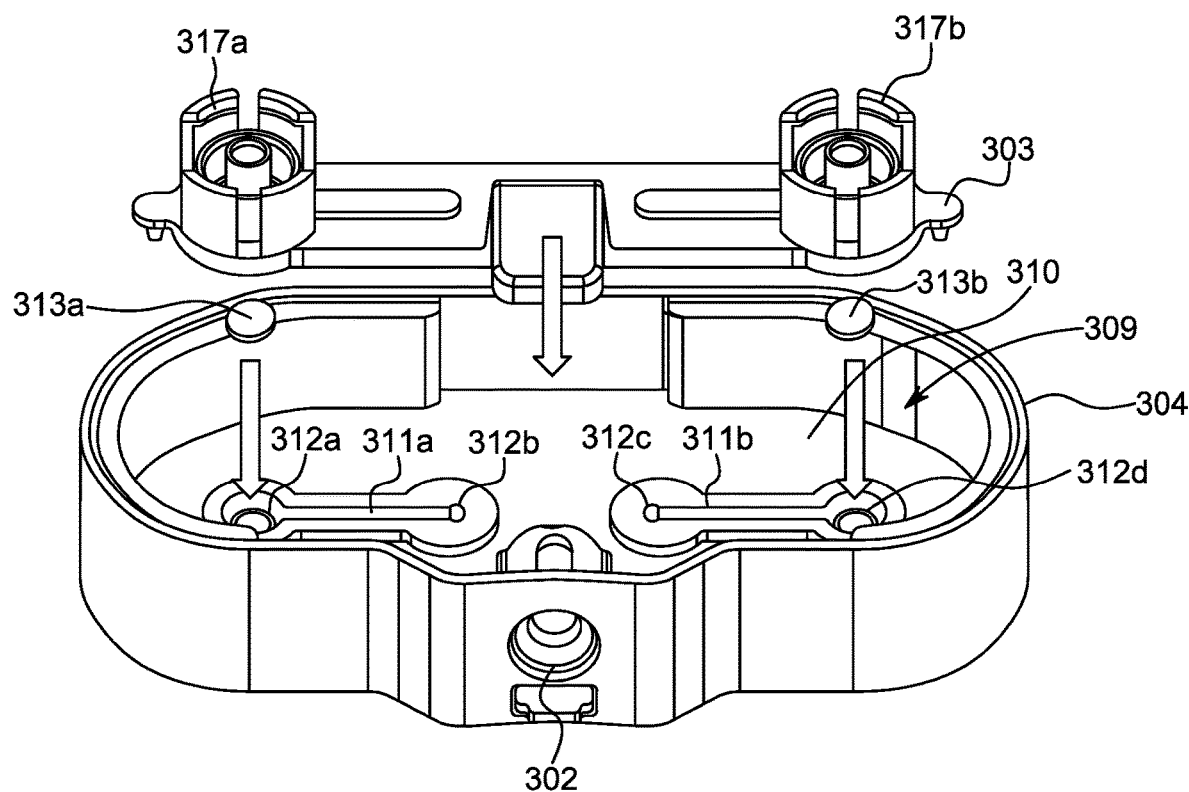
FIG. 17B is an exploded bottom perspective view of a lower body member and a middle body member of the manifold assembly of FIG. 16 according to an embodiment.
Figure 17C:
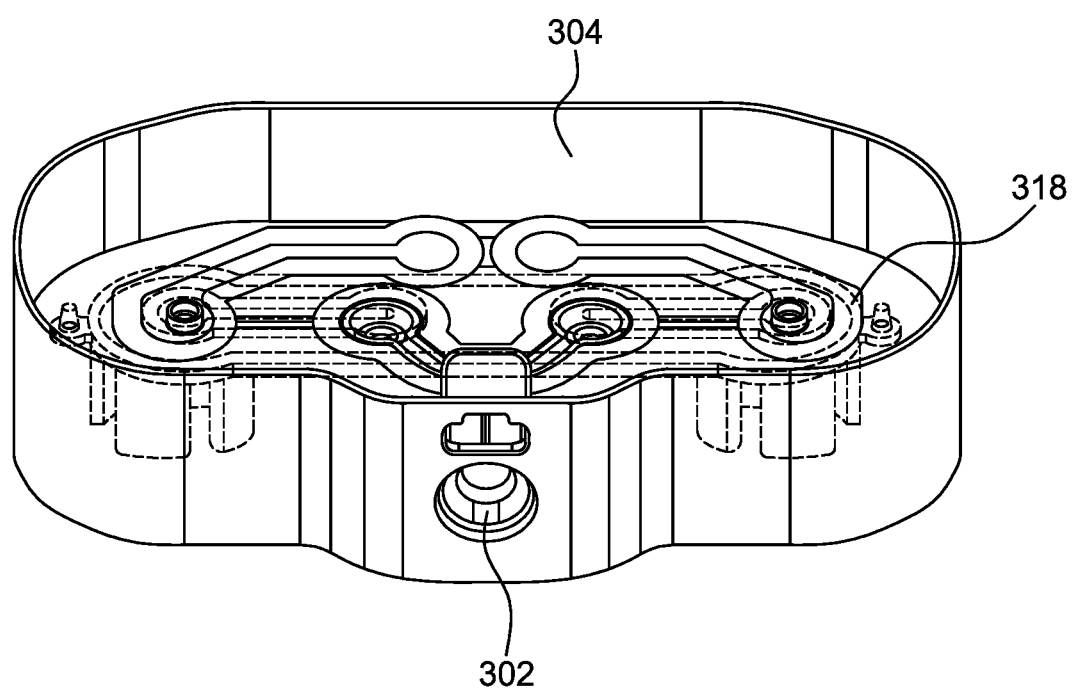
FIG. 17C is a top perspective view of the lower body member and middle body member of FIG. 17B according to an embodiment.
Figure 17D:
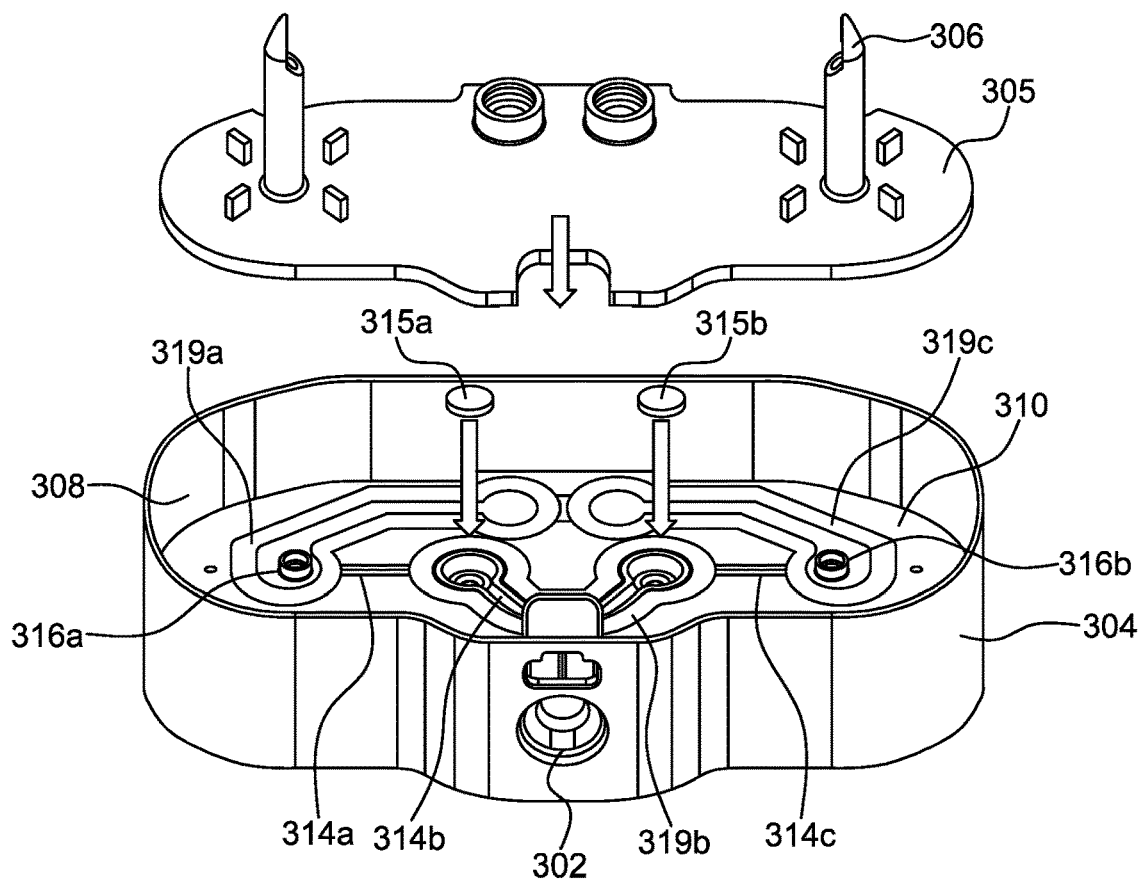
FIG. 17D is an exploded view of an upper body member and a middle body member of the manifold assembly of FIG. 16 according to an embodiment.

With reference to FIGS. 17B and 17D, the middle body member 304 defines an upper cavity 308 (FIG. 17D) and a lower cavity 309 (FIG. 17B). The upper cavity 308 is configured to receive or attach to the upper body member 305 and the lower cavity 309 is configured to receive or attach to the lower body member 303. The middle body member 304 also defines the outlet opening 302 that is configured to connect the manifold assembly 300 to single-patient use fluid lines that are fluidly connected to the vasculature of the patient. The middle body member 304 also includes a dividing plate 310 that separates the upper cavity 308 from the lower cavity 309. As shown in FIG. 17B, at least a pair of fluid paths 311a, 311b may be defined in the lower surface of the dividing plate 310. Each fluid path 311a, 311b may define a pair of ports 312a-312d in the dividing plate 310. A check valve diaphragm 313a, 313b may be provided in two of the ports 312a, 312d on the bottom surface of dividing plate 310. In another example, instead of providing the check valve diaphragms 313a, 313b, a floating disc valve may be provided in two of the ports 312a, 312d on the bottom surface of the dividing plate 310. Several examples of such a floating disc valve are disclosed and illustrated in U.S. Pat. No. 9,526,829, which disclosure is incorporated by reference in its entirety.

As shown in FIG. 17D, a plurality of fluid paths 314a-314c may be defined in an upper surface of the dividing plate 310. One fluid path 314b may define two ports to receive check valve diaphragms 315a, 315b. In another example, instead of providing the check valve diaphragms 315a, 315b, a floating disc valve may be provided in the two ports 312b, 312c, such as the examples of floating disc valves disclosed in U.S. Pat. No. 9,526,829. The two ports 312b, 312e may also be defined by the fluid paths 311a, 311b. Two additional ports 316a, 316b may be defined in the dividing plate 310 with the ports 312a, 312d to establish fluid communication with the spike members 306 of the upper body member 305 and connectors 317a, 317b of the lower body member 303, described below.

As shown in FIG. 17B, the lower body member 303 may include connectors 317a, 317b configured to establish fluid communication between the manifold assembly 300 and the syringe assemblies. Other examples of suitable connectors are described in U.S. Provisional Application No. 62/259, 891. The connectors 317a, 317b are provided in fluid communication with the ports 312a, 312d defined in the dividing plate 310. The check valve diaphragms 313a, 313b are positioned between the connectors 317a, 317b and the ports 312a, 312d. The check valve diaphragms 313a, 313b permit fluid to flow from the spike members 306 on the manifold assembly 300 to the syringe assemblies, but does not allow fluid to backflow from the syringe assemblies through the connectors 317a, 317b in the manifold assembly 300 and into the single- or multi-dose bottles or bags attached to the spike members 306. Instead, during injection of fluid into a patient, the fluid is directed back into the manifold assembly 300 against the bottom surface of the check valve diaphragms 313a, 313b, through the fluid path 311a, 311b, ports 312a, 312b, check valve diaphragms 315a, 315b, and along fluids path 314b defined in an upper surface of the dividing plate 310, and through the outlet 302 to the patient line. The check valve diaphragms 315a, 315b direct the fluid to the outlet 302 and prevent backflow to the connectors 317a, 317k. The fluid paths 311a, 311b, the ports 312b, 312c, and the fluid path 314b establish fluid communication between the connectors 317a, 317b and the outlet 302.

Figure 17E:
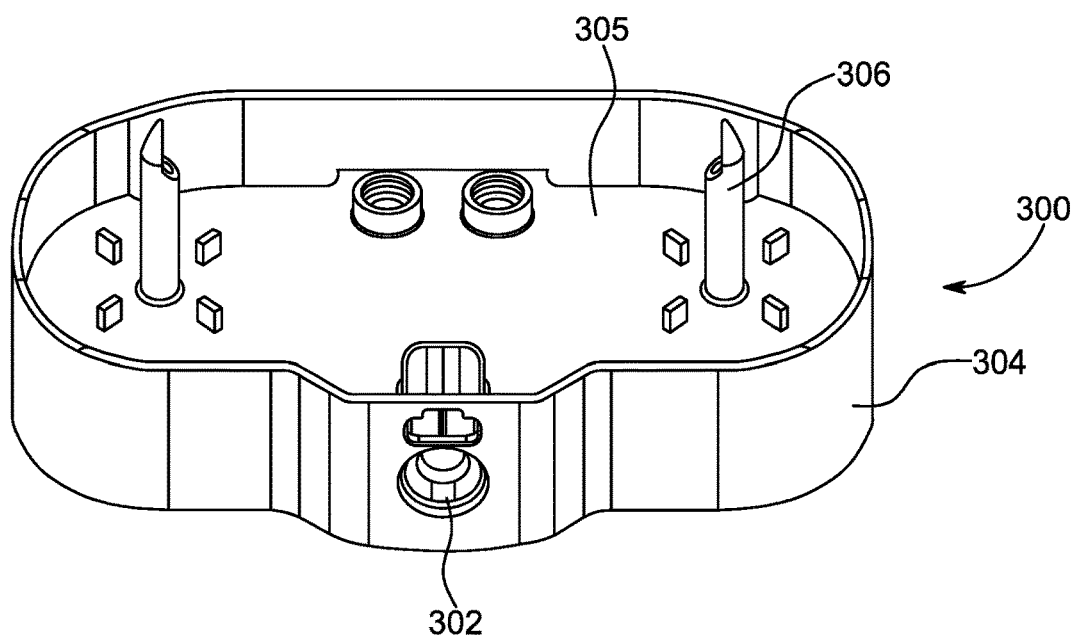
FIG. 17E is a front perspective view of a fully-assembled manifold assembly of FIG. 16 according to an embodiment.
Figure 18A:
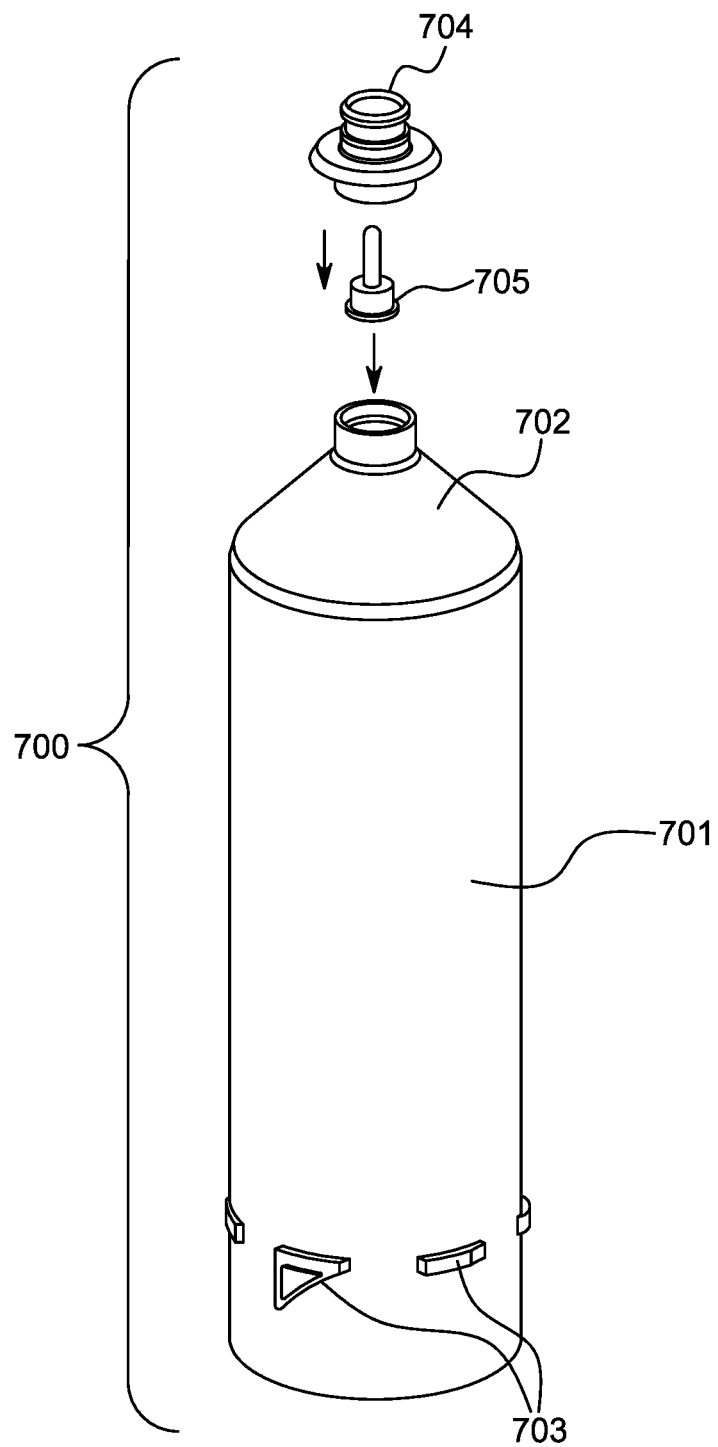
FIG. 18A is an exploded view of a syringe assembly according to an embodiment.
Figure 18B:
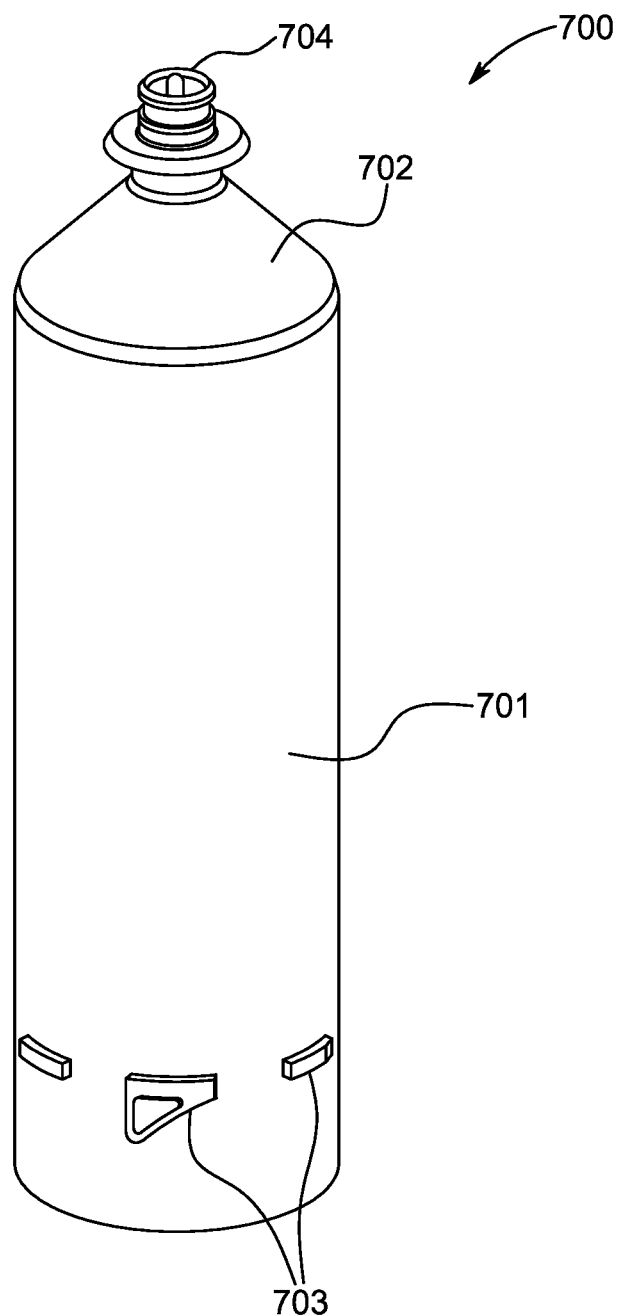
FIG. 18B is a front perspective view of the syringe assembly of FIG. 18A according to an embodiment.
Figure 18C:
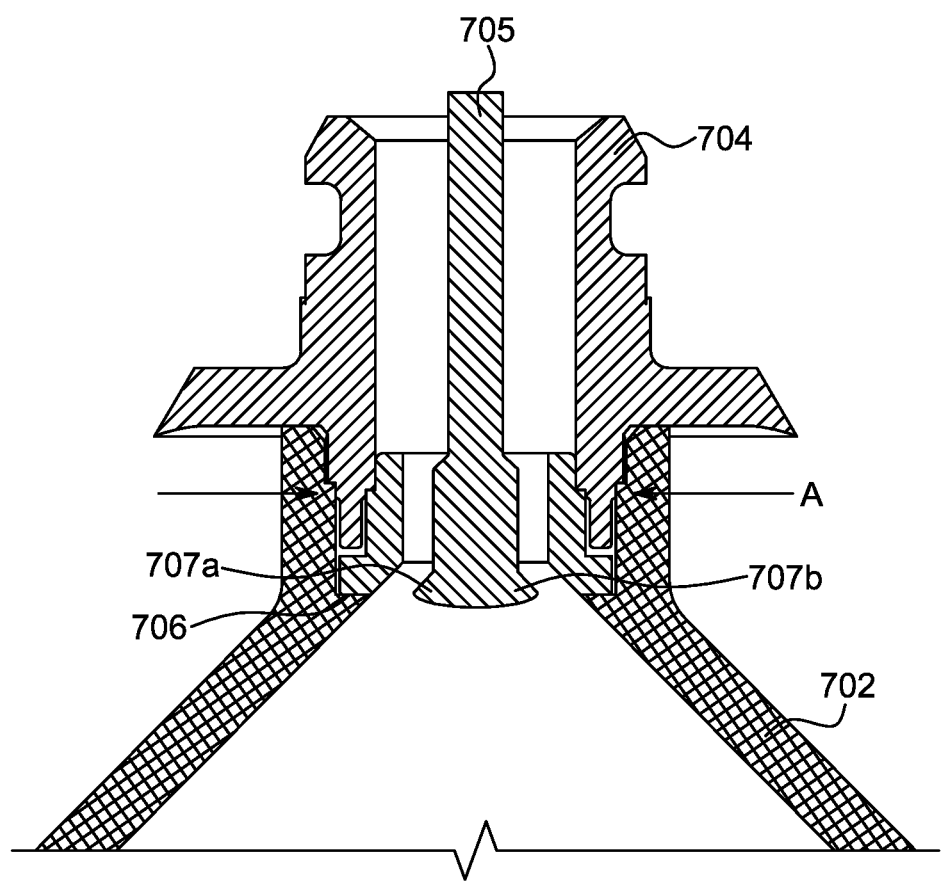
FIG. 18C is an isolated view of an adapter and flow directing ring in the syringe assembly of FIG. 18A according to an embodiment.

With reference to FIGS. 1.7B-17E, the assembly of the manifold assembly 300 is described according to one example. In a first step, the check valve diaphragms 313a, 313b are inserted into the ports 312a, 312d defined in the dividing plate 310. In a next step, the lower body member 303 is positioned on the middle body member 304. Subsequently, the lower body member 303 and the middle body member 304 are flipped over. The lower body member 303 is then welded or adhered to the middle body member 304 along a weld or adhesion path 318 that encircles the fluid paths 311a, 311b defined in the dividing plate 310 to prevent fluid from flowing out of the fluid paths 311a, 311b. In one example, laser welding may be used to create a concentrated heat source in the respective components permitting the components to weld to and form with one another. In one example, the laser welding direction may be directed from a top surface of the dividing plate 310, through the dividing plate 310, and into the lower body member 303. Alternatively, an appropriate heat weld protocol or application of an appropriate adhesive may secure the lower body member 303 to dividing plate 310. Next, the check valve diaphragms 315a, 315b are positioned in the ports defined in the fluid path 314a, 314c on the top side of dividing plate 310. The fluid paths 314a, 314e, and 314b are then welded or adhered through a top surface of the dividing plate 310 along weld paths 319a-319c for example by laser welding, heat welding or other adhesive process. The upper body member 305 is then pressed on the middle body member 304 to form the two elements together based on adhesion created by the welding or adhesion process. The resulting manifold assembly 300 is illustrated in FIG. 17E.

With reference 18A-18C, an example of a syringe assembly 700 of one of the one or more syringes 253 configured for connection to the manifold assembly 300 is described.

The syringe assembly 700 includes a barrel 701, a conical distal end 702, and locking features 703, as described for example in U.S. Pat. Nos. 6,652,489; 9,173,995; and 9,199, 033, configured to secure the syringe assembly 700 in an injector 100. A plunger (not shown) may be slidably contained within the barrel 701 to draw in and expel fluid from the syringe assembly 700. The syringe assembly 700 may also include an adapter 704 and flow directing assembly 705 provided in an opening defined in the conical distal end 702. Examples of suitable adapters and flow directing assemblies are described in International Application Publication Nos. WO 2017/091635; WO 2017/091636; and WO 2017/091643, the disclosures of which are incorporated herein by this reference. The adapter 704 is configured for connection with the connectors 317a, 317b of the manifold assembly 300. The flow directing assembly 705 may be seated on a protrusion 706 extending from an inner surface of the conical distal end 702 such that a portion of the flow directing assembly 705 is held between the protrusion 706 and the adapter 704. The adapter 704 may be positioned on top of the flow directing assembly 705 within the conical distal end 702. The adapter 704 and the flow directing assembly 705 may be connected to one another and the conical distal end 702 using welding or other adhesion directed along line A, for example by a laser welding or other process as described herein. The flow directing assembly 705 is configured to direct fluid being drawn into the syringe assembly 700 along the inner walls of the barrel 701 to avoid creating turbulent flow in the syringe assembly 700. The fluid is directed along the inner walls of the barrel 701 to create more laminar flow into the barrel 701, which avoids the creation of air bubbles from turbulent flow in the syringe assembly 700. The flow directing assembly 705 may include a main body having two angled surfaces 707a, 707b that direct the fluid towards the inner walls of the barrel 701.

Figure 19A:
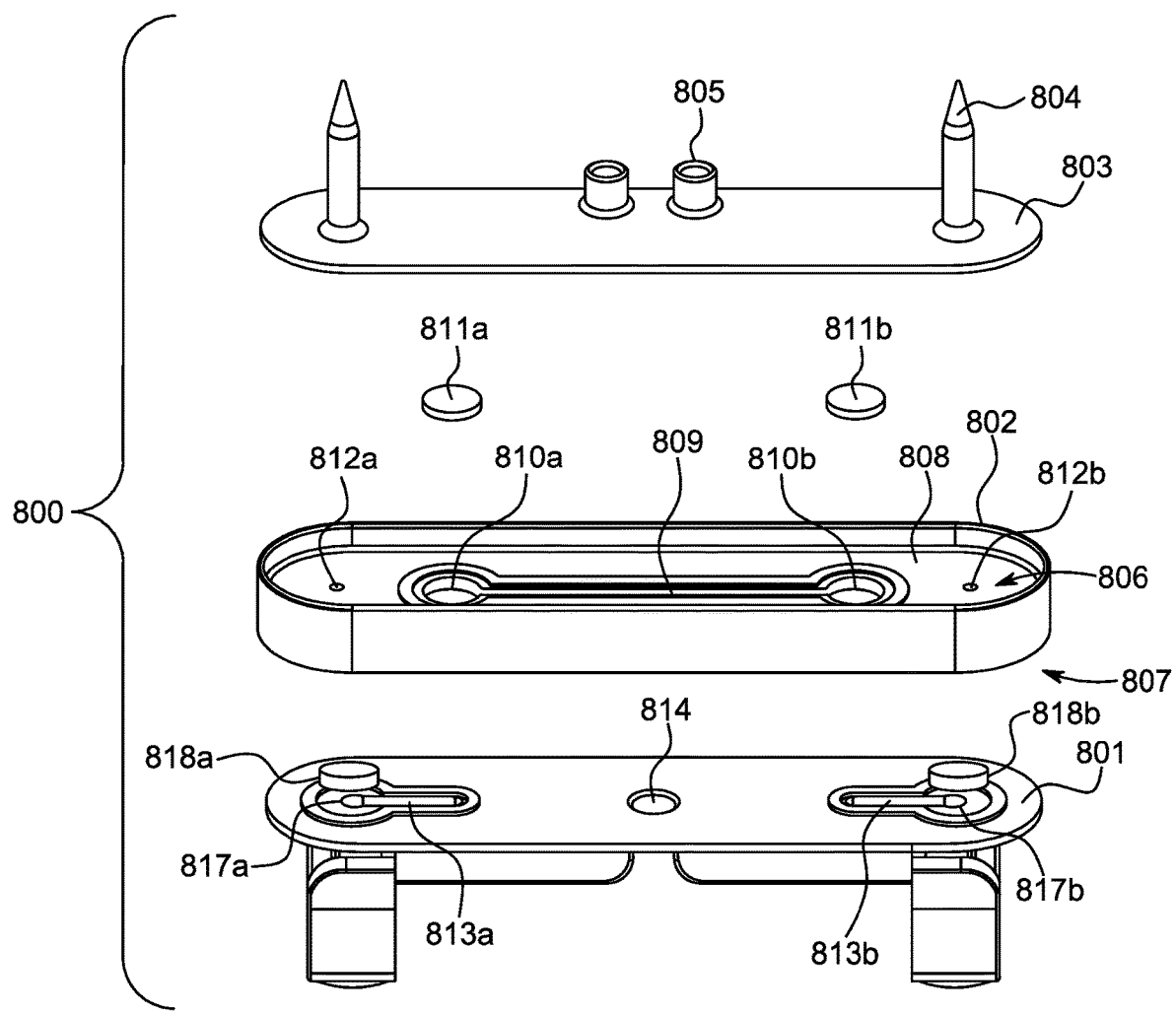
FIG. 19A is an exploded view of a single-use manifold assembly according to an embodiment.

With reference to FIGS. 19A-19D, a manifold assembly 800 according to an example suitable for use with a single-dose injector is described. The manifold assembly 800 includes a lower body member 801, a middle body member 802, and an upper body member 803. The lower body member 801 is configured to fit within or attach to a lower portion of the middle body member 802. The upper body member 803 is configured to fit within or attached to an upper portion of the middle body member 802. As shown in FIG. 19A, the upper body member 803 includes at least one fluid conducting element, such as a spike member 804, used to pierce or connect to a septum or cap on a fluid bottle. It is to be understood that fluid conducting members other than a spike member can also be used, such as a fluid connector. The spike member 804 creates fluid communication between the fluid bottle and the manifold assembly 800. The spike member 804 may have a pointed end used to pierce the septum or cap on the fluid bottle and at least one fluid path to allow fluid communication between the fluid bottle or bag and the manifold assembly 800. In one example the at least one spike member 804 may further include a second fluid path to allow air or other gas to pass into the fluid bottle or bag to equalize the pressure in the interior of the fluid bottle or bag. The upper body member 803 may also define at least one port 805.

The middle body member 802 defines an upper cavity 806 and a lower cavity 807. The upper cavity 806 is configured to receive the upper body member 803 and the lower cavity 807 is configured to receive the lower body member 801. The middle body member 802 also includes a dividing plate 808 that separates the upper cavity 806 from the lower cavity 807. As shown in FIG. 19A, a fluid path 809 may be defined in the upper surface of the dividing plate 808. The fluid path 809 may define a pair of ports 810a, 810b in the dividing plate 808. A check valve diaphragm 811a, 811b may be provided in the ports 810a, 810b to prevent backflow from the patient line into the syringes. In another example, instead of providing the check valve diaphragms 811a, 811b, a floating disc valve may be provided in two of the ports 810a, 810b. Several examples of such a floating disc valve are disclosed and illustrated in U.S. Pat. No. 9,526,829. Two additional ports 812a, 812b may be defined in the dividing plate 808. The ports 812a, 812b are in fluid communication with the spike members 804 of the upper body member 803. Ports 812a, 812b may have check valve diaphragms 818a, 818b on a bottom portion to prevent backflow of fluid from the syringe into the fluid bottles or bags. It is also contemplated that floating disc valves may be used in place of the check valve diaphragms 818a, 818b.

The lower body member 801 may define at least two fluid paths 813a, 813b. The lower body member 801 also defines an outlet port 814 in fluid communication with fluid path 809 through which fluid may be directed to the patient. The outlet port 814 may be defined between the fluid paths 813a, 813b. Fluid from a fluid bottle or bag spiked on the upper body member 803 is directed through the ports 812a, 812b in the middle body member 802 and into the syringes through fluid paths 817a, 817b defined in the lower body member 801 during a syringe filling process. The fluid is then expelled from the syringes into the fluid paths 813a, 813b, through ports 810a, 810b in the dividing plate 808 and check valve diaphragm 811a, 811b into fluid path 809 defined in the middle body member 802. The check valve diaphragms 811a, 811b allow flow of fluid from the fluid paths 813a, 813b defined in the lower body member 801 to the fluid path 809 defined in the middle body member 802, but prevents backflow of fluid in a reverse direction (i.e., flow from the fluid path 809 defined in the middle body member 802 to the fluid paths 813a, 813b defined in the lower body member 801). After the fluid flows into the fluid path 809, the fluid is directed out through the outlet port 814 defined in the lower body member 801 to the patient via a patient line (not shown), such as a catheter or IV line.

Figure 19B:
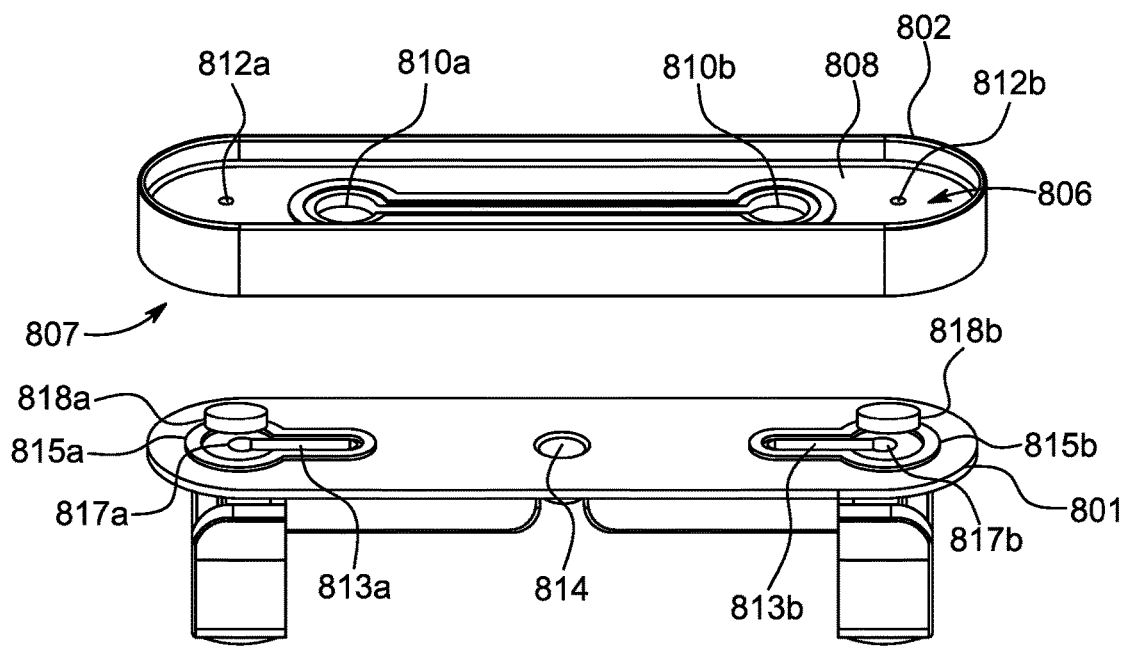
FIG. 19B is an exploded view of a lower body member and a middle body member of the manifold assembly of FIG. 19A according to an embodiment.
Figure 19C:
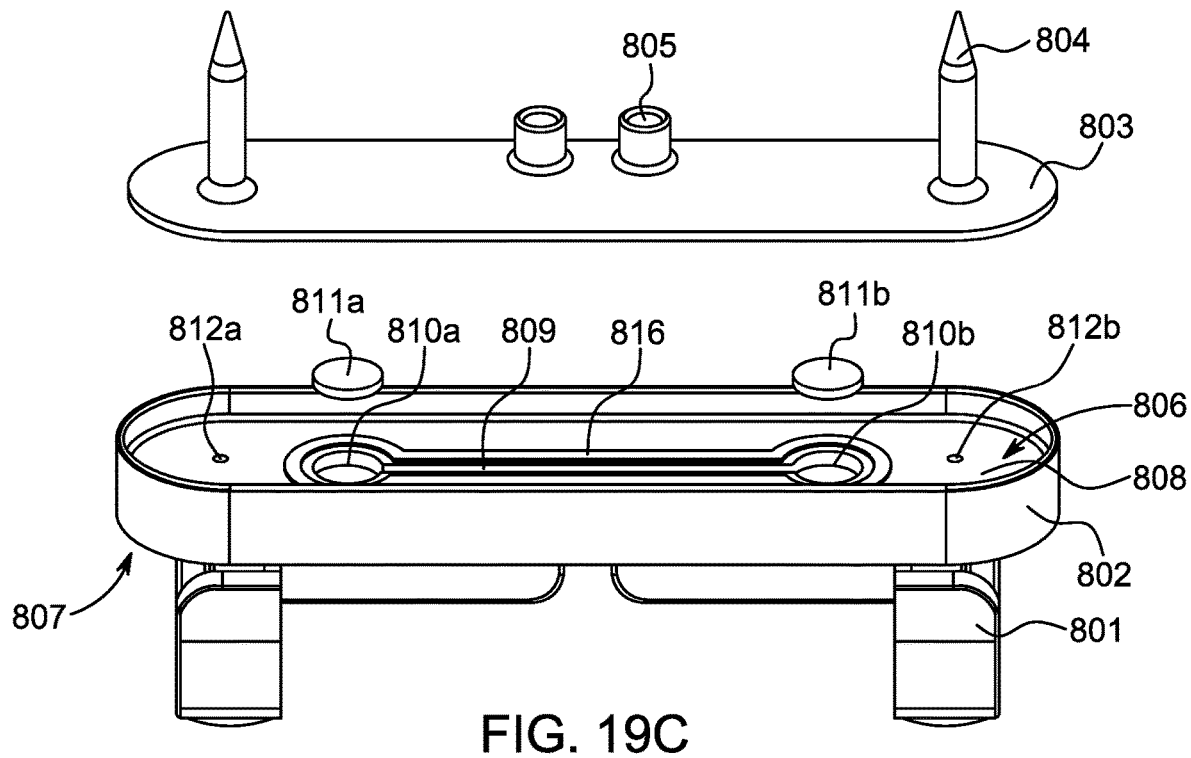
FIG. 19C is an exploded view of the manifold assembly of FIG. 19A according to an embodiment showing welding paths.
Figure 19D:
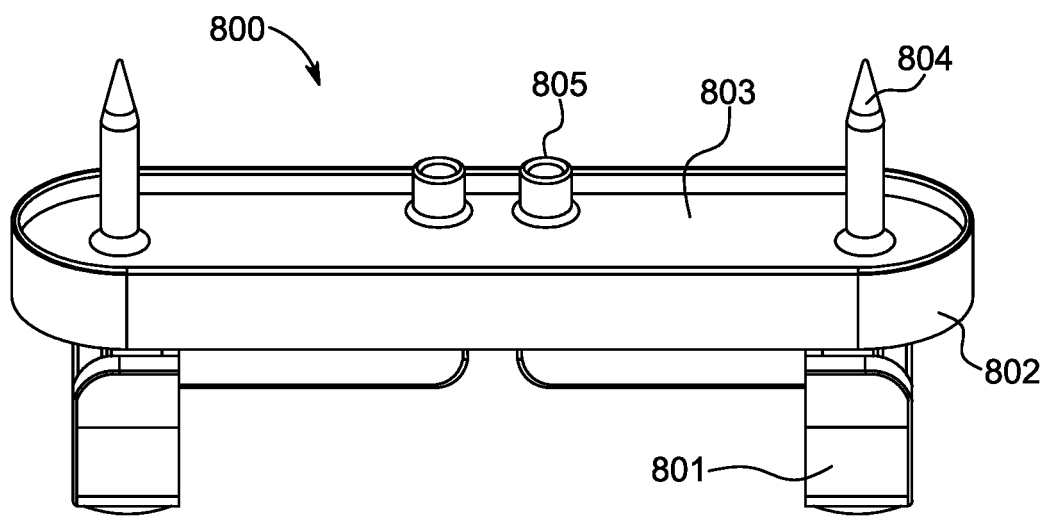
FIG. 19D is a front perspective view of a fully-assembled manifold assembly shown in FIG. 19A according to an embodiment.

With reference to FIGS. 19B-19D, a method of assembling the manifold assembly 800 is described. In a first step, the lower body member 801 is positioned within the lower cavity 807 defined by the middle body member 802. Check valve diaphragms are inserted into lower face of ports 812a, 812b and lower body member 801 is then welded or adhered to the dividing plate 808 of the middle body member 802, for example by laser welding. In one example, the welding or adhesion is performed along weld/adhesion paths 815a, 815b directed around the fluid paths 813a, 813b defined in the lower body member 801 to permit adhesion of the lower body member 801 to the middle body member 802. The check valve diaphragms 811a, 811b are then inserted into the ports 810a, 801b defined in the dividing plate 808. The upper body member 803 is then positioned against the dividing plate 808 in the upper cavity 806 of the middle body member 802. The upper body member 803 is then welded or adhered to the middle body member 802 along a weld path 816 that is directed around the fluid path 809 and ports 810a, 810b, for example by laser welding. After these steps have been completed, the manifold assembly 800 (FIG. 19O) is been fully assembled.

While various examples of the injector 100, manifold assemblies 300, 800, and syringe assemblies 700 were provided in the description, those skilled in the art may make modifications and alterations to these examples without departing from the scope and spirit of the disclosure. For example, it is understood that this disclosure contemplates that, to the extent possible, one or more features of any example may be combined with one or more features of any other example. Accordingly, the foregoing description is intended to be illustrative rather than restrictive. The disclosure herein is defined by the appended claims. All changes to the disclosure that fall within the meaning and range of equivalency of the claims are to be embraced within their scope.

What is claimed is:

1. A syringe manifold for a fluid injector assembly, the syringe manifold comprising:
    an upper body member, the upper body member comprising at least one spike member for piercing a fluid container;
    a middle body member defining an upper cavity and a lower cavity, wherein the upper body member is connected with the upper cavity of the middle body member, and wherein the middle body member further comprises:
        at least one first fluid path defined in an upper surface of the middle body member;
        at least one second fluid path defined in a lower surface of the middle body member;
        at least one first port defined by the at least one first fluid path;
        at least one second port defined by the at least one first fluid path and the at least one second fluid path; and
        an outlet for connection of the syringe manifold to at least one fluid delivery device; and
    a lower body member connected with the lower cavity of the middle body member, the lower body member comprising at least one connector for connection of the lower body member to a syringe assembly,
    wherein the at least one first port on the middle body member establishes fluid communication between the at least one spike member and the at least one connector, and wherein the at least one first fluid path, the at least one second fluid path, and the at least one second port establish fluid communication between the at least one connector and the outlet of the middle body member.

2. The syringe manifold of 1, wherein the at least one spike member comprises two spike members, and wherein the at least one connector of the lower body member comprises two connectors.

3. The syringe manifold of claim 2, wherein the at least one one second fluid path defined in the lower surface of the middle body member comprises two second fluid paths in the lower surface of the middle body member, and wherein the at least one first port and the at least one second port of the middle body member comprise two first ports and two second ports, respectively, extending through the middle body member.

4. The syringe manifold of claim 1, wherein the at least one first port is defined at a first end of the at least one second fluid path defined in the lower surface of the middle body member, and wherein the at least one second port is defined at a second, opposing end of the at least one second fluid path defined in the lower surface of the middle body member.

5. The syringe manifold of claim 1, further comprising at least one check valve diaphragm in each of the at least one first port and the at least one second port.

6. The syringe manifold of claim 5, wherein the at least one check valve diaphragm of the at least one fluid port comprises a first check valve diaphragm positioned between the at least one spike member and the at least one connector and permits fluid flow from the at least one spike member to the at least one connector and prevents fluid flow from the at least one connector to the at least one spike member, and wherein the at least one check valve diaphragm of the at least one second port comprises a second check valve diaphragm positioned between the at least one connector and the outlet of the middle body member and permits fluid flow from the at least one connector to the outlet and prevents fluid flow from the outlet to the at least one connector.

7. The syringe manifold of claim 1, wherein at least one floating disc valve is provided in each of the at least one first port and the at least one second port.

8. The syringe manifold of claim 7, wherein the at least one first floating disc valve is positioned between the at least one spike member and the at least one connector and permits fluid flow from the at least one spike member to the at least one connector and prevents fluid flow from the at least one connector to the at least one spike member, and at least one second floating disc valve is positioned between the at least one connector and the outlet of the middle body member and permits fluid flow from the at least one connector to the outlet and prevents fluid flow from the outlet to the at least one connector.

9. The syringe manifold of claim 1, wherein at least one of the upper body member and the lower body member are welded or adhered to the middle body member.

10. The syringe manifold of claim 1, further comprising at least one syringe connected to the at least one connector.

11. A syringe manifold for a fluid injector assembly, the syringe manifold comprising:
    an upper body member comprising at least one spike member for piercing a septum of at least one fluid container;
    a middle body member defining an upper cavity and a lower cavity, wherein the upper body member is connected with the upper cavity of the middle body member, the middle body member further comprising:
        at least one fluid path in an upper surface of the middle body member;
        at least one first port defined by a dividing plate of the middle body member; and
        at least one second port defined by the at least one fluid path; and
    a lower body member connected with the lower cavity of the middle body member, the lower body member comprising:
        at least one connector for connecting the lower body member to a syringe assembly;
        at least one second fluid path; and
        an outlet for connecting the syringe manifold to at least one fluid delivery device,
    wherein the at least one first port defined by the dividing plate of the middle body member establishes fluid communication between the at least one spike member and the at least one connector, and wherein the at least one second fluid path defined in the lower body member, the at least one first port defined by the dividing plate of the middle body member, the at least one fluid path defined in the upper surface of the middle body member, and the at least one second port defined in the middle body member establish fluid communication between the at least one connector and the outlet of the lower body member.

12. The syringe manifold of claim 11, wherein the at least one spike member of the upper body member comprises two spike members, and wherein the at least one connector of the lower body member comprises two connectors.

13. The syringe manifold of claim 12, wherein the at least one second fluid path of the lower body member comprises two second fluid paths, and wherein the at least one first port of the middle body member comprises two first ports extending through the middle body member and the at least one second fluid port comprises two second fluid ports.

14. The syringe manifold of claim 11, wherein the at least one first port provided in the middle body member is positioned adjacent a first end of the at least one second fluid path defined in the lower body member, and wherein the at least one second port provided in the middle body member is positioned adjacent a second, opposing end of the at least one second fluid path defined in the lower body member.

15. The syringe manifold of claim 11, further comprising at least one check valve diaphragm or floating disc valve positioned between the at least one spike member of the upper body member and the at least one connector of the lower body member.

16. The syringe manifold of claim 11, further comprising at least one syringe connected to the at least one connector.

\* \* \* \* \*

UNITED STATES PATENT AND TRADEMARK OFFICE
CERTIFICATE OF CORRECTION

PATENT NO. : 11,376,360 B2
APPLICATION NO. : 16/316810
DATED : July 5, 2022
INVENTOR(S) : Savio et al.

It is certified that error appears in the above-identified patent and that said Letters Patent is hereby corrected as shown below:

In the Specification
In Column 1, Line 66, delete "adjacent" and insert -- adjacent IV --, therefor.
In Column 8, Line 1, delete "170" and insert -- 17D --, therefor.
In Column 8, Line 21, delete "190" and insert -- 19D --, therefor.
In Column 10, Line 17, delete "PCT/US12/374891" and insert -- PCT/US12/37491 --, therefor.
In Column 11, Line 48, delete "injector stand 118" and insert -- support portion 118 --, therefor.
In Column 14, Line 6, delete "In" and insert -- In non-limiting --, therefor.
In Column 15, Line 65, delete "hulk" and insert -- bulk --, therefor.
In Column 16, Line 35, delete "253, in" and insert -- 253. In --, therefor.
In Column 18, Line 36, delete "use" and insert -- use it --, therefor.
In Column 20, Line 49, delete "312a-312d" and insert -- 312a, 312d --, therefor.
In Column 20, Line 67, delete "312e" and insert -- 312c --, therefor.
In Column 21, Line 30, delete "317k" and insert -- 317b. --, therefor.
In Column 21, Line 34, delete "1.7B-17E," and insert -- 17B-17E, --, therefor.
In Column 21, Line 57, delete "314e," and insert -- 314c, --, therefor.
In Column 21, Line 65, delete "18A-18C," and insert -- to FIGS. 18A-18C, --, therefor.
In Column 23, Line 55, delete "801b" and insert -- 810b --, therefor.
In Column 23, Line 63, delete "190)" and insert -- 19D) --, therefor.
In Column 23, Line 63, delete "is been" and insert -- has been --, therefor.

In the Claims
In Column 24, Line 44, in Claim 2, delete "1," and insert -- claim 1, --, therefor.

Signed and Sealed this
Thirty-first Day of January, 2023

Katherine Kelly Vidal
*Director of the United States Patent and Trademark Office*